United States Patent
Van de Cotte et al.

(10) Patent No.: US 10,670,027 B2
(45) Date of Patent: Jun. 2, 2020

(54) DETERMINING QUALITY OF GAS FOR ROTATING EQUIPMENT IN A PETROCHEMICAL PLANT OR REFINERY

(71) Applicant: UOP LLC, Des Plaines, IL (US)

(72) Inventors: Michael Van de Cotte, Palatine, IL (US); Ian G. Horn, Streamwood, IL (US)

(73) Assignee: UOP LLC, Des Plaines, IL (US)

( * ) Notice: Subject to any disclaimer, the term of this patent is extended or adjusted under 35 U.S.C. 154(b) by 16 days.

(21) Appl. No.: 15/935,935

(22) Filed: Mar. 26, 2018

(65) Prior Publication Data

US 2018/0283392 A1 Oct. 4, 2018

Related U.S. Application Data

(60) Provisional application No. 62/477,819, filed on Mar. 28, 2017.

(51) Int. Cl.
*F04D 27/00* (2006.01)
*G01N 33/00* (2006.01)
(Continued)

(52) U.S. Cl.
CPC ......... *F04D 27/001* (2013.01); *F04D 17/122* (2013.01); *F04D 27/0292* (2013.01);
(Continued)

(58) Field of Classification Search
CPC .. F04D 27/001; F04D 27/0292; F04D 29/122; F04D 17/122; F04D 29/083; G01N 33/0075; G05B 15/02
See application file for complete search history.

(56) References Cited

U.S. PATENT DOCUMENTS 4,380,146 A 4/1983 Yannone .............. 60/39.281
4,775,460 A 10/1988 Reno
(Continued)

FOREIGN PATENT DOCUMENTS

EP 2746884 A1 6/2014 ............ G05B 23/02
EP 2801937 A1 11/2014 ............ G06Q 10/06
(Continued)

OTHER PUBLICATIONS

Daniel Goebel, Dry Gas Seal Contamination During Operation and Pressurization Hold, [online], Feb. 2016, [retrieved on Jun. 19, 2019]. Retrieved from <https://core.ac.uk/download/pdf/84815277.pdf> (Year: 2016).*

(Continued)

*Primary Examiner* — Thomas C Lee
*Assistant Examiner* — Charles Cai

(57) ABSTRACT

A plant or refinery may include equipment such as condensers, regenerators, distillation columns, rotating equipment, compressors, pumps, turbines, or the like. Different operating methods may impact deterioration in equipment condition, thereby prolonging equipment life, extending production operating time, or providing other benefits. Mechanical or digital sensors may be used for monitoring equipment to determine whether problems are developing. For example, sensors may be used in conjunction with one or more system components to perform invariant mapping, monitor system operating characteristics, and/or predict pressure, volume, surges, reactor loop fouling, gas quality, or the like. An operating condition (e.g., of one or more pieces of equipment in the plant or refinery) may be adjusted to prolong equipment life or avoid equipment failure.

17 Claims, 25 Drawing Sheets

(51) Int. Cl.
  *G05B 15/02* (2006.01)
  *F04D 17/12* (2006.01)
  *F04D 27/02* (2006.01)
  *F04D 29/08* (2006.01)
  *F04D 29/12* (2006.01)

(52) U.S. Cl.
  CPC ......... *F04D 29/083* (2013.01); *F04D 29/122* (2013.01); *G01N 33/0075* (2013.01); *G05B 15/02* (2013.01)

(56) References Cited

U.S. PATENT DOCUMENTS

| | | |
|---|---|---|
| 4,795,545 A | 1/1989 | Schmidt |
| 5,077,252 A | 12/1991 | Owen et al. ................ 502/43 |
| 5,605,435 A | 2/1997 | Haugen ................ 137/514 |
| 5,666,297 A | 9/1997 | Britt et al. ................ 364/578 |
| 5,817,517 A | 10/1998 | Perry et al. ................ 436/55 |
| 6,038,540 A | 3/2000 | Krist et al. ................ 705/8 |
| 6,392,114 B1 | 5/2002 | Shields et al. ................ 582/719 |
| 6,760,716 B1 | 7/2004 | Ganesamoorthi et al. ..... 706/21 |
| 6,772,044 B1 | 8/2004 | Mathur et al. ................ 700/204 |
| 6,795,798 B2 | 9/2004 | Eryurek et al. ................ 702/188 |
| 7,006,889 B2 | 2/2006 | Mathur et al. ................ 700/204 |
| 7,067,333 B1 | 6/2006 | Pasadyn et al. ................ 438/5 |
| 7,133,807 B2 | 11/2006 | Karasawa ................ 702/188 |
| 7,151,966 B1 | 12/2006 | Baier et al. ................ 700/19 |
| 7,246,039 B2 | 7/2007 | Moorhouse ................ 702/185 |
| 7,313,447 B2 | 12/2007 | Hsuing et al. ................ 700/9 |
| 7,415,357 B1 | 8/2008 | Stluka et al. ................ 702/6 |
| 7,567,887 B2 | 7/2009 | Emigholz et al. ................ 702/182 |
| 7,742,833 B1 | 6/2010 | Herbst et al. ................ 700/108 |
| 7,877,596 B2 | 1/2011 | Foo Kune et al. ................ 713/153 |
| 7,925,979 B2 | 4/2011 | Forney et al. ................ 715/733 |
| 7,936,878 B2 | 5/2011 | Kune et al. ................ 380/270 |
| 7,979,192 B2 | 7/2011 | Morrison et al. |
| 7,995,526 B2 | 8/2011 | Liu et al. ................ 370/329 |
| 8,050,889 B2 | 11/2011 | Fluegge et al. ................ 702/182 |
| 8,055,371 B2 | 11/2011 | Sanford et al. ................ 700/108 |
| 8,111,619 B2 | 2/2012 | Liu et al. ................ 370/229 |
| 8,204,717 B2 | 6/2012 | McLaughlin et al. ........ 702/188 |
| 8,244,384 B2 | 8/2012 | Pachner et al. ................ 700/30 |
| 8,280,057 B2 | 10/2012 | Budampati et al. ........ 380/270 |
| 8,352,049 B2 | 1/2013 | Hsiung et al. |
| 8,385,436 B2 | 2/2013 | Holm et al. ................ 375/260 |
| 8,428,067 B2 | 4/2013 | Budampati et al. ..... 370/395.21 |
| 8,458,778 B2 | 6/2013 | Budampati et al. ................ 726/6 |
| 8,571,064 B2 | 10/2013 | Kore et al. ................ 370/469 |
| 8,644,192 B2 | 2/2014 | Budampati et al. ........ 370/255 |
| 8,811,231 B2 | 8/2014 | Budampati et al. ........ 370/255 |
| 8,923,882 B2 | 12/2014 | Gandhi et al. ................ 455/455 |
| 9,134,717 B2 | 9/2015 | Trnka |
| 9,166,667 B2 | 10/2015 | Thanikachalam |
| 9,176,498 B2 | 11/2015 | Baramov |
| 9,751,817 B2 | 9/2017 | Jani et al. |
| 9,864,823 B2 | 1/2018 | Horn et al. |
| 9,968,899 B1 | 5/2018 | Gellaboina et al. |
| 10,095,200 B2 | 10/2018 | Horn et al. |
| 10,107,295 B1 | 10/2018 | Brecheisen |
| 10,180,680 B2 | 1/2019 | Horn et al. |
| 10,183,266 B2 | 1/2019 | Victor et al. |
| 10,222,787 B2 | 3/2019 | Romatier et al. |
| 10,328,408 B2 | 6/2019 | Victor et al. |
| 2002/0123864 A1 | 9/2002 | Eryurek et al. ................ 702/188 |
| 2002/0179495 A1 | 12/2002 | Heyse et al. ................ 208/137 |
| 2003/0147351 A1 | 8/2003 | Greenlee ................ 370/232 |
| 2004/0079392 A1 | 4/2004 | Kuechler ................ 134/22.19 |
| 2004/0099572 A1 | 5/2004 | Evans ................ 208/113 |
| 2004/0109788 A1 | 6/2004 | Li et al. |
| 2004/0204775 A1 | 10/2004 | Keyes ................ 705/30 |
| 2004/0220689 A1 | 11/2004 | Mathur et al. ................ 700/97 |
| 2004/0220778 A1 | 11/2004 | Imai et al. ................ 702/188 |
| 2005/0027721 A1 | 2/2005 | Saenz ................ 707/100 |
| 2005/0216209 A1 | 9/2005 | Evans ................ 702/45 |
| 2006/0020423 A1 | 1/2006 | Sharpe, Jr. ................ 702/183 |
| 2006/0133412 A1 | 6/2006 | Callaghan ................ 370/465 |
| 2006/0259163 A1 | 11/2006 | Hsiung et al. ................ 700/30 |
| 2007/0020154 A1 | 1/2007 | Evans ................ 422/139 |
| 2007/0059159 A1 | 3/2007 | Hjerpe ................ 415/117 |
| 2007/0059838 A1 | 3/2007 | Morrison et al. ................ 436/55 |
| 2007/0091824 A1 | 4/2007 | Budampati et al. ........ 370/255 |
| 2007/0091825 A1 | 4/2007 | Budampati et al. ........ 370/255 |
| 2007/0185664 A1 | 8/2007 | Tanaka ................ 702/56 |
| 2007/0192078 A1 | 8/2007 | Nasle et al. ................ 703/14 |
| 2007/0250292 A1 | 10/2007 | Alagappan et al. ........ 702/184 |
| 2007/0271452 A1 | 11/2007 | Foo Kune et al. ................ 713/150 |
| 2008/0086322 A1 | 4/2008 | Wallace ................ 705/1 |
| 2008/0130902 A1 | 6/2008 | Foo Kune et al. ................ 380/286 |
| 2008/0217005 A1 | 9/2008 | Stluka et al. ................ 166/250.01 |
| 2008/0282606 A1 | 11/2008 | Plaza et al. |
| 2009/0059786 A1 | 3/2009 | Budampati et al. ........ 370/230 |
| 2009/0060192 A1 | 3/2009 | Budampati et al. ........ 380/270 |
| 2009/0064295 A1 | 3/2009 | Budampati et al. ................ 726/6 |
| 2009/0201899 A1 | 8/2009 | Liu et al. ................ 370/338 |
| 2009/0245286 A1 | 10/2009 | Kore et al. ................ 370/475 |
| 2009/0268674 A1 | 10/2009 | Liu et al. ................ 370/329 |
| 2010/0014599 A1 | 1/2010 | Holm et al. ................ 375/260 |
| 2010/0108567 A1 | 5/2010 | Medoff ................ 208/49 |
| 2010/0125347 A1 | 5/2010 | Martin et al. ................ 700/31 |
| 2010/0158764 A1 | 6/2010 | Hedrick ................ 422/134 |
| 2010/0262900 A1 | 10/2010 | Romatier et al. ................ 715/219 |
| 2011/0112659 A1 | 5/2011 | Pachner et al. ................ 700/29 |
| 2011/0152590 A1 | 6/2011 | Sadler et al. ................ 585/313 |
| 2011/0152591 A1 | 6/2011 | Sadler et al. ................ 585/313 |
| 2011/0311014 A1 | 12/2011 | Hottovy et al. ................ 376/283 |
| 2012/0083933 A1 | 4/2012 | Subbu et al. ................ 700/291 |
| 2012/0095808 A1 | 4/2012 | Kattapuram et al. ........ 705/7.37 |
| 2012/0104295 A1 | 5/2012 | Do et al. ................ 251/129.01 |
| 2012/0121376 A1 | 5/2012 | Huis in Het Veld ............ 415/1 |
| 2012/0123583 A1 | 5/2012 | Hazen et al. |
| 2012/0197616 A1 | 8/2012 | Trnka ................ 703/6 |
| 2012/0259583 A1 | 10/2012 | Noboa et al. |
| 2013/0029587 A1 | 1/2013 | Gandhi et al. ................ 455/7 |
| 2013/0031960 A1* | 2/2013 | Delrahim ................ F01D 11/06 73/40.5 R |
| 2013/0079899 A1 | 3/2013 | Baramov ................ 700/32 |
| 2013/0090088 A1 | 4/2013 | Chevsky et al. |
| 2013/0094422 A1 | 4/2013 | Thanikachalam ............ 370/312 |
| 2013/0253898 A1 | 9/2013 | Meagher et al. ................ 703/18 |
| 2013/0270157 A1 | 10/2013 | Ferrara ................ 208/48 AA |
| 2013/0311437 A1 | 11/2013 | Stluka et al. ................ 707/706 |
| 2013/0327052 A1* | 12/2013 | O'Neill ................ F02C 6/18 60/772 |
| 2014/0026598 A1 | 1/2014 | Trawicki ................ 62/56 |
| 2014/0074273 A1 | 3/2014 | Mohideen et al. ............ 700/98 |
| 2014/0114039 A1 | 4/2014 | Benham et al. ........ 526/348.5 |
| 2014/0131027 A1 | 5/2014 | Chir ................ 165/300 |
| 2014/0163275 A1 | 6/2014 | Yanagawa et al. ........ 585/319 |
| 2014/0179968 A1 | 6/2014 | Yanagawa et al. ........ 585/476 |
| 2014/0212978 A1 | 7/2014 | Sharpe, Jr. et al. ............ 436/6 |
| 2014/0294683 A1 | 10/2014 | Siedler ................ 422/129 |
| 2014/0294684 A1 | 10/2014 | Siedler ................ 422/129 |
| 2014/0296058 A1 | 10/2014 | Sechrist et al. ................ 502/53 |
| 2014/0309756 A1 | 10/2014 | Trygstad ................ 700/31 |
| 2014/0337256 A1 | 11/2014 | Varadi et al. ................ 706/12 |
| 2015/0059714 A1 | 3/2015 | Bernards ................ 123/568.11 |
| 2015/0077263 A1 | 3/2015 | Ali et al. ................ 340/679 |
| 2015/0078970 A1 | 3/2015 | Iddir et al. ................ 422/218 |
| 2015/0098862 A1 | 4/2015 | Lok et al. ................ 422/49 |
| 2015/0158789 A1 | 6/2015 | Keusenkothen ................ 60/780 |
| 2015/0185716 A1 | 7/2015 | Wichmann et al. ........ 700/287 |
| 2015/0276208 A1 | 10/2015 | Maturana et al. ............ 700/274 |
| 2015/0330571 A1 | 11/2015 | Beuneken ................ 141/4 |
| 2016/0033941 A1 | 2/2016 | T et al. ................ 700/81 |
| 2016/0098037 A1 | 4/2016 | Zornio et al. ................ 700/20 |
| 2016/0147204 A1 | 5/2016 | Wichmann et al. ........ 700/287 |
| 2016/0237910 A1 | 8/2016 | Saito |
| 2016/0260041 A1 | 9/2016 | Horn et al. |
| 2016/0291584 A1 | 10/2016 | Horn et al. |
| 2016/0292188 A1 | 10/2016 | Horn et al. |
| 2016/0292325 A1 | 10/2016 | Horn et al. |
| 2017/0009932 A1 | 1/2017 | Oh |
| 2017/0058213 A1 | 3/2017 | Oprins ................ 585/303 |
| 2017/0082320 A1 | 3/2017 | Wang |

(56) References Cited

U.S. PATENT DOCUMENTS

| | | | |
|---|---|---|---|
| 2017/0107188 A1* | 4/2017 | Kawaguchi | C07D 301/10 |
| 2017/0284410 A1* | 10/2017 | Sharpe, Jr. | F04D 27/0223 |
| 2017/0315543 A1 | 11/2017 | Horn et al. | |
| 2017/0323038 A1 | 11/2017 | Horn et al. | |
| 2017/0352899 A1 | 12/2017 | Asai | |
| 2018/0046155 A1 | 2/2018 | Horn et al. | |
| 2018/0081344 A1 | 3/2018 | Romatier et al. | |
| 2018/0082569 A1 | 3/2018 | Horn et al. | |
| 2018/0121581 A1 | 5/2018 | Horn et al. | |
| 2018/0122021 A1 | 5/2018 | Horn et al. | |
| 2018/0155638 A1 | 6/2018 | Al-Ghamdi | 208/79 |
| 2018/0155642 A1 | 6/2018 | Al-Ghamdi et al. | |
| 2018/0197350 A1 | 7/2018 | Kim | |
| 2018/0275690 A1 | 9/2018 | Lattanzio et al. | |
| 2018/0275691 A1 | 9/2018 | Lattanzio et al. | |
| 2018/0275692 A1 | 9/2018 | Lattanzio et al. | |
| 2018/0280914 A1 | 10/2018 | Victor et al. | |
| 2018/0280917 A1 | 10/2018 | Victor et al. | |
| 2018/0282633 A1 | 10/2018 | Van de Cotte et al. | |
| 2018/0282634 A1 | 10/2018 | Van de Cotte et al. | |
| 2018/0282635 A1 | 10/2018 | Van de Cotte et al. | |
| 2018/0283368 A1 | 10/2018 | Van de Cotte et al. | |
| 2018/0283392 A1 | 10/2018 | Van de Cotte et al. | |
| 2018/0283404 A1 | 10/2018 | Van de Cotte et al. | |
| 2018/0283811 A1 | 10/2018 | Victor et al. | |
| 2018/0283812 A1 | 10/2018 | Victor et al. | |
| 2018/0283813 A1 | 10/2018 | Victor et al. | |
| 2018/0283815 A1 | 10/2018 | Victor et al. | |
| 2018/0283816 A1 | 10/2018 | Victor et al. | |
| 2018/0283818 A1 | 10/2018 | Victor et al. | |
| 2018/0284705 A1 | 10/2018 | Van de Cotte et al. | |
| 2018/0286141 A1 | 10/2018 | Van de Cotte et al. | |
| 2018/0311609 A1 | 11/2018 | McCool et al. | |
| 2018/0362862 A1 | 12/2018 | Gellaboina et al. | |
| 2018/0363914 A1 | 12/2018 | Faiella et al. | |
| 2018/0364747 A1 | 12/2018 | Charr et al. | |
| 2019/0002318 A1 | 1/2019 | Thakkar et al. | |
| 2019/0003978 A1 | 1/2019 | Shi et al. | |
| 2019/0015806 A1 | 1/2019 | Gellaboina et al. | |
| 2019/0041813 A1 | 2/2019 | Horn et al. | |
| 2019/0083920 A1 | 3/2019 | Bjorklund et al. | |
| 2019/0101336 A1 | 4/2019 | Victor et al. | |
| 2019/0101342 A1 | 4/2019 | Victor et al. | |
| 2019/0101907 A1 | 4/2019 | Charr et al. | |
| 2019/0102966 A1* | 4/2019 | Lorenz | G01N 29/02 |
| 2019/0108454 A1 | 4/2019 | Banerjee et al. | |
| 2019/0120810 A1 | 4/2019 | Kumar et al. | |
| 2019/0151814 A1 | 5/2019 | Victor et al. | |
| 2019/0155259 A1 | 5/2019 | Romatier et al. | |

FOREIGN PATENT DOCUMENTS

| | | | | |
|---|---|---|---|---|
| WO | WO 2001/060951 A1 | 8/2001 | | C10G 51/04 |
| WO | WO 2009/046095 A1 | 4/2009 | | G06F 11/00 |
| WO | WO 2014/042508 A1 | 3/2014 | | G06Q 50/04 |
| WO | WO 2014/123993 A1 | 8/2014 | | G06F 17/00 |
| WO | WO 2016/141128 A1 | 9/2016 | | G06Q 10/06 |

OTHER PUBLICATIONS

Chistof Huber, Density and Concentration Measurement Application for Novel MEMS-based Micro Densitometer for Gas, [online], 2016, [retrieved on Jun. 19, 2019]. Retrieved from <https://www.ama-science.org/proceedings/getFile/ZwZ1BD==> (Year: 2016).*

Lotters, Real-time Composition Determination of Gas Mixtures, [online], 2015, [retrieved on Jun. 19, 2019]. Retrieved from <https://www.ama-science.org/proceedings/getFile/ZwN0Zj==> (Year: 2015).*

Jul. 12, 2018—(WO) International Search Report & Written Opinion—PCT/US2018/024903.

U.S. Appl. No. 15/935,827: Non-Final Office Action (dated Jun. 10, 2019).

U.S. Appl. No. 15/935,898: Non-Final Office Action (dated Jun. 19, 2019).

U.S. Appl. No. 15/935,872: Non-Final Office Action (dated Jun. 25, 2019).

U.S. Appl. No. 15/058,658, filed Mar. 3, 2015, Ian G. Horn Zak Alzein Paul Kowalczyk Christophe Romatier, System and Method for Managing Web-Based Refinery Performance Optimization Using Secure Cloud Computing.

U.S. Appl. No. 15/640,120, filed Mar. 30, 2015, Ian G. Horn Zak Alzein Paul Kowalczyk Christophe Romatier, Evaluating Petrochemical Plant Errors to Determine Equipment Changes for Optimized.

U.S. Appl. No. 15/851,207, filed Mar. 27, 2017, Louis A. Lattanzio Alex Green Ian G. Horn Matthew R. Wojtowicz, Operating Slide Valves in Petrochemical Plants or Refineries.

U.S. Appl. No. 15/851,343, filed Dec. 21, 2017, Louis A. Lattanzio Alex Green Ian G. Horn Matthew R. Wojtowicz, Early Prediction and Detection of Slide Valve Sticking in Petrochemical Plants or Refineries.

U.S. Appl. No. 15/851,360, filed Mar. 27, 2017, Louis A. Lattanzio Alex Green Ian G. Horn Matthew R. Wojtowicz, Measuring and Determining Hot Spots in Slide Valves for Petrochemical Plants or Refineries.

U.S. Appl. No. 15/853,689, filed Mar. 30, 2015, Ian G. Horn Zak Alzein Paul Kowalczyk Christophe Romatier, Cleansing System for a Feed Composition Based on Environmental Factors.

U.S. Appl. No. 15/858,767, filed Dec. 28, 2017, Ian G. Horn Zak Alzein Paul Kowalczyk Christophe Romatier, Chemical Refinery Performance Optimization.

U.S. Appl. No. 15/899,967, filed Feb. 20, 2018, Joel Kaye, Developing Linear Process Models Using Reactor Kinetic Equations.

U.S. Appl. No. 15/935,827, filed Mar. 28, 2017, Michael R. Van de Cotte Ian G. Horn, Rotating Equipment in a Petrochemical Plant or Refinery.

U.S. Appl. No. 15/935,847, filed Mar. 28, 2017, Michael R. Van de Cotte Ian G. Horn, Rotating Equipment in a Petrochemical Plant or Refinery.

U.S. Appl. No. 15/935,872, filed Mar. 28, 2017, Michael R. Van de Cotte Ian G. Horn, 3744early Surge Detection of Rotating Equipment in a Petrochemical Plant or Refinery.

U.S. Appl. No. 15/935,898, filed Mar. 28, 2017, Michael R. Van de Cotte Ian G. Horn, Reactor Loop Fouling Monitor for Rotating Equipment in a Petrochemical Plant or Refinery.

U.S. Appl. No. 15/935,920, filed Mar. 28, 2017, Michael R. Van de Cotte Ian G. Horn, Sensor Location for Rotating Equipment in a Petrochemical Plant or Refinery.

U.S. Appl. No. 15/935,935, filed Mar. 28, 2017, Michael R. Van de Cotte Ian G. Horn, Determining Quality of Gas for Rotating Equipment in a Petrochemical Plant or Refinery.

U.S. Appl. No. 15/935,950, filed Mar. 28, 2017, Michael R. Van de Cotte Ian G. Horn, Determining Quality of Gas for Rotating Equipment in a Petrochemical Plant or Refinery.

U.S. Appl. No. 15/935,957, filed Mar. 28, 2017, Michael R. Van de Cotte Ian G. Horn, Using Molecular Weight and Invariant Mapping to Determine Performance of Rotating Equipment in a Petrochemical Plant or Refinery.

U.S. Appl. No. 15/937,484, filed Mar. 28, 2017, Sanford A. Victor Phillip F. Daly Ian G. Horn, Detecting and Correcting Maldistribution in Heat Exchangers in a Petrochemical Plant or Refinery.

U.S. Appl. No. 15/937,499, filed Mar. 28, 2017, Sanford A. Victor Phillip F. Daly Ian G. Horn, Detecting and Correcting Cross-Leakage in Heat Exchangers in a Petrochemical Plant or Refinery.

U.S. Appl. No. 15/937,517, filed Mar. 28, 2017, Sanford A. Victor Phillip F. Daly Ian G. Horn, Strain Gauges and Detecting Pre-Leakage in Heat Exchangers in a Petrochemical Plant or Refinery.

U.S. Appl. No. 15/937,535, filed Mar. 28, 2017, Sanford A. Victor Phillip F. Daly Ian G. Horn, Detecting and Correcting Thermal Stresses in Heat Exchangers in a Petrochemical Plant or Refinery.

U.S. Appl. No. 15/937,588, filed Mar. 28, 2017, Sanford A. Victor Phillip F. Daly Ian G. Horn, Detecting and Correcting Problems in Liquid Lifting in Heat Exchangers.

U.S. Appl. No. 15/937,602, filed Mar. 28, 2017, Sanford A. Victor Phillip F. Daly Ian G. Horn, Air-Cooled Heat Exchangers.

U.S. Appl. No. 15/937,614, filed Mar. 28, 2017, Sanford A. Victor Phillip F. Daly Ian G. Horn, Wet-Cooled Heat Exchanger.

(56) References Cited

OTHER PUBLICATIONS

U.S. Appl. No. 15/937,624, filed Mar. 28, 2017, Sanford A. Victor Phillip F. Daly Ian G. Horn, Heat Exchangers in a Petrochemical Plant or Refinery.

U.S. Appl. No. 15/963,840, filed Apr. 28, 2017, Ryan McCool Chad E. Bjorklund Jorge Charr Luk Verhulst, Remote Monitoring of Adsorber Process Units.

U.S. Appl. No. 15/972,974, filed Jun. 20, 2017, Jorge Charr Kevin Carnes Ralph Davis Donald A. Eizenga Christina L. Haasser James W. Harris Raul A. Ohaco Daliah Papoutsis, Incipient Temperature Excursion Mitigation and Control.

U.S. Appl. No. 15/979,421, filed May 14, 2018, Mahesh K. Gellaboina Louis A. Lattanzio, Catalyst Transfer Pipe Plug Detection.

U.S. Appl. No. 16/007,669, filed Jun. 28, 2017, Yili Shi Daliah Papoutsis Jonathan Andrew Tertel, Process and Apparatus to Detect Mercaptans in a Caustic Stream.

U.S. Appl. No. 16/011,600, filed Jun. 19, 2017, Theodore Peter Faiella Colin J. Deller Raul A. Ohaco, Remote Monitoring of Fired Heaters.

U.S. Appl. No. 16/011,614, filed Jun. 19, 2017, Mahesh K. Gellaboina Michael Telly Seth Huber Danielle Schindlbeck, Catalyst Cycle Length Prediction Using Eigen Analysis.

U.S. Appl. No. 16/015,579, filed Jun. 28, 2017, Killol H. Thakkar Robert W. Brafford Eric C. Tompkins, Process and Apparatus for Dosing Nutrients to a Bioreactor.

U.S. Appl. No. 16/133,623, filed Sep. 18, 2017, Chad E. Bjorklund Jeffrey Guenther Stephen Kelley Ryan McCool, Remote Monitoring of Pressure Swing Adsorption Units.

U.S. Appl. No. 16/140,770, filed Oct. 20, 2017, Dinesh Kumar KN Soumendra Mohan Banerjee, System and Method to Optimize Crude Oil Distillation or Other Processing by Inline Analysis of Crude Oil Properties.

U.S. Appl. No. 16/148,763, filed Oct. 2, 2017, Jorge Chan Bryan J. Egolf Dean E. Rende Mary Wier Guy B. Woodle Carol Zhu, Remote Monitoring of Chloride Treaters Using a Process Simulator Based Chloride Distribution Estimate.

U.S. Appl. No. 16/151,086, filed Oct. 5, 2017, Soumendra Mohan Banerjee Deepak Bisht Priyesh Jayendrakumar Jani Krishna Mani Gautam Pandey, Harnessing Machine Learning & Data Analytics for a Real Time Predictive Model for a Fcc Pre-Treatment Unit.

U.S. Appl. No. 16/154,138, filed Oct. 8, 2018, Raul A. Ohaco Jorge Charr, High Purity Distillation Process Control With Multivariable and Model Predictive Control (Mpc) and Fast Response Analyzer.

U.S. Appl. No. 16/154,141, filed Oct. 8, 2018, Ian G. Horn Zak Alzein Paul Kowalczyk Christophe Romatier, System and Method for Improving Performance of a Plant With a Furnace.

U.S. Appl. No. 16/215,101, filed Dec. 10, 2018, Louis A. Lattanzio Christopher Schindlbeck, Delta Temperature Control of Catalytic Dehydrogenation Process Reactors.

U.S. Appl. No. 16/252,021, filed Sep. 16, 2016, Christophe Romatier Zak Alzein Ian G. Horn Paul Kowalczyk David Rondeau, Petrochemical Plant Diagnostic System and Method for Chemical Process Model Analysis.

U.S. Appl. No. 16/253,181, filed Mar. 28, 2017, Ian G. Horn Phillip F. Daly Sanford A. Victor, Detecting and Correcting Vibration in Heat Exchangers.

U.S. Appl. No. 16/363,406, filed Mar. 30, 2018, Louis A. Lattanzio Abhishek Pednekar, Catalytic Dehydrogenation Reactor Performance Index.

\* cited by examiner

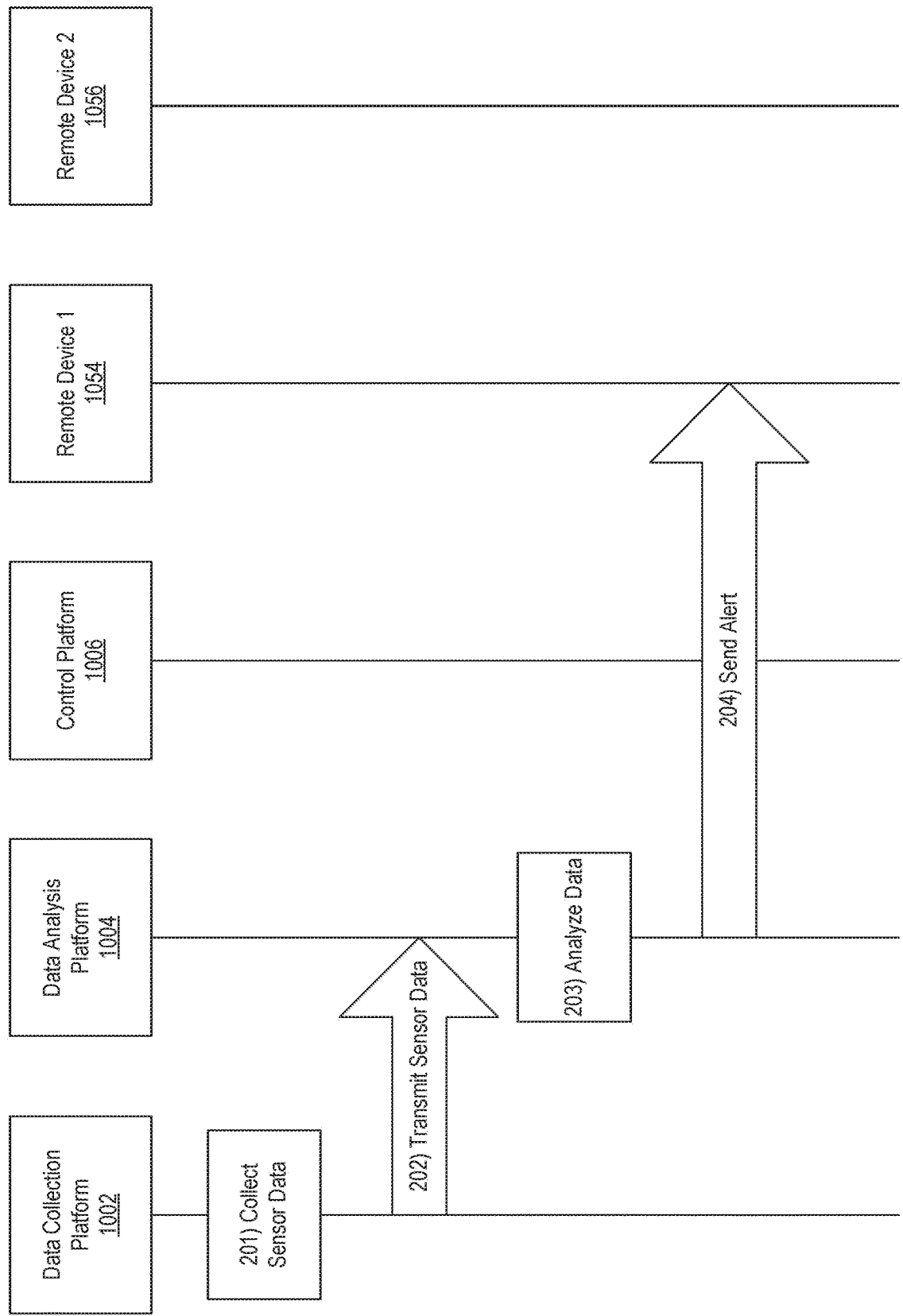

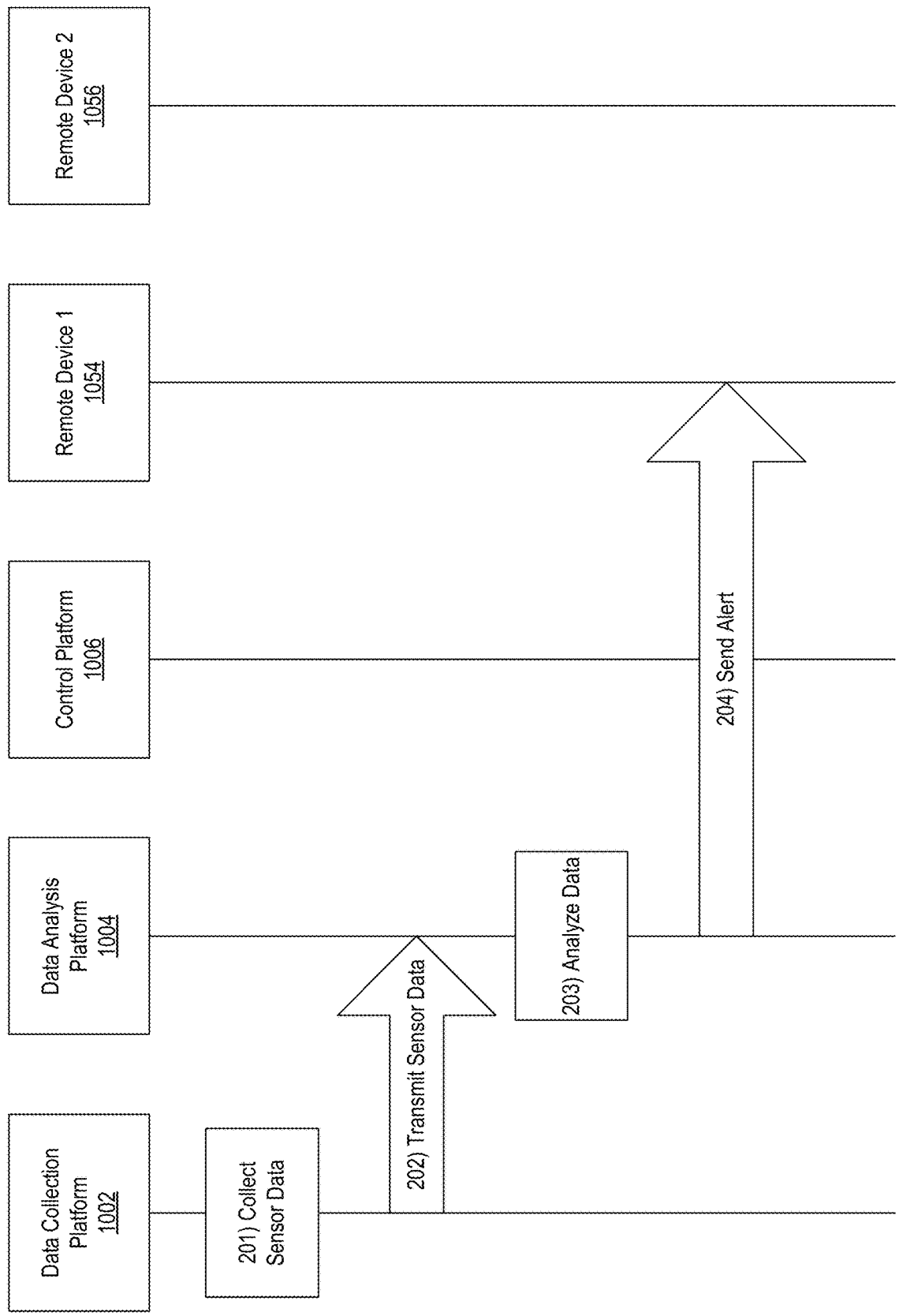

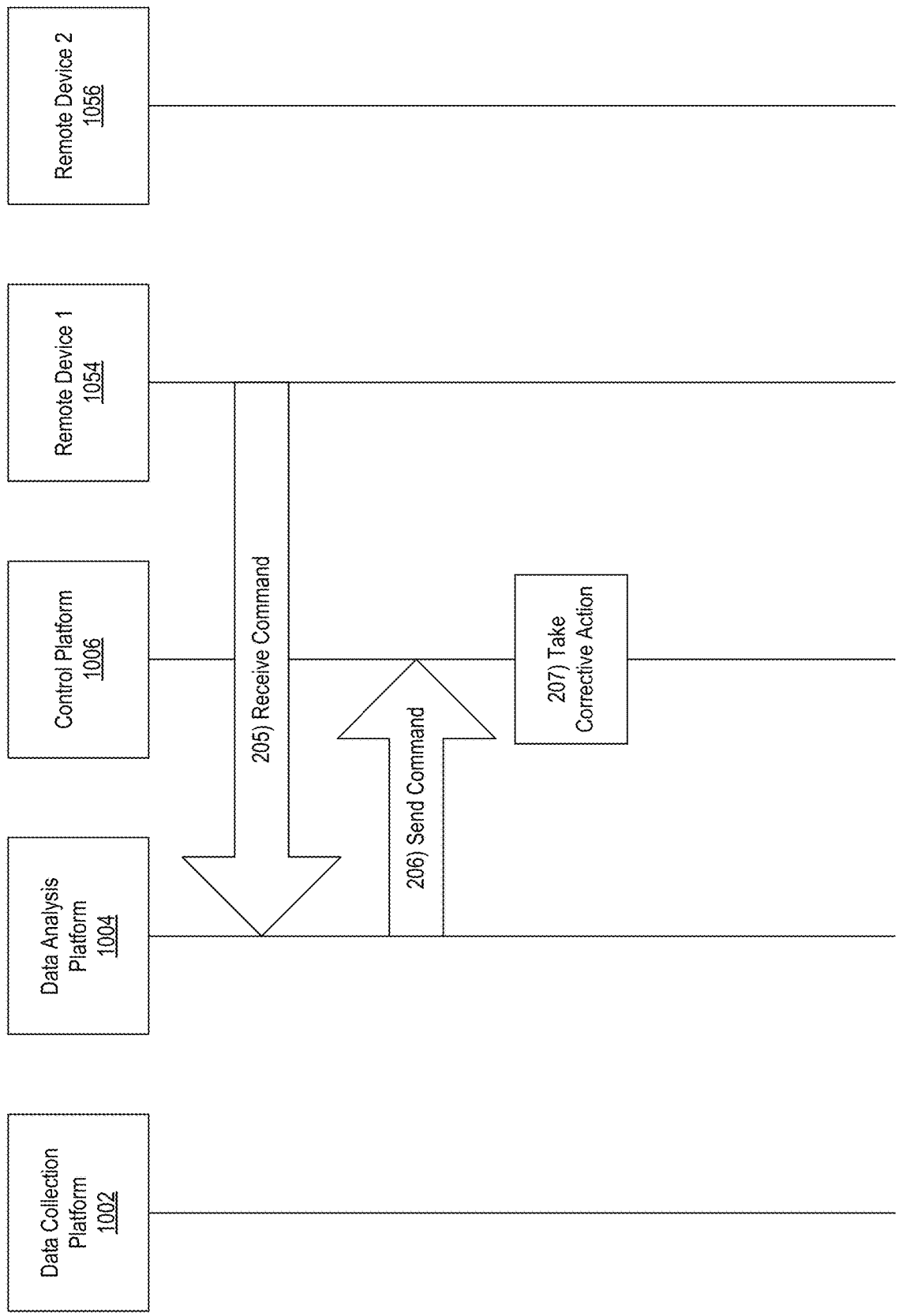

DETERMINING QUALITY OF GAS FOR ROTATING EQUIPMENT IN A PETROCHEMICAL PLANT OR REFINERY

CROSS-REFERENCE TO RELATED APPLICATION

This application claims the benefit of priority under 35 U.S.C. § 119(e) of U.S. Provisional Application No. 62/477,819, filed Mar. 28, 2017, which is incorporated by reference in its entirety.

FIELD

The present disclosure is related to a method and system for improving the performance of components that make up operations in a plant, such as a carbonaceous processing plant, a chemical plant, a petrochemical plant, or a refinery. Typical plants may be those that provide catalytic dehydrogenation or hydrocarbon cracking.

BACKGROUND

A plant or refinery may include one or more pieces of equipment for performing a process. Equipment may break down over time, and need to be repaired or replaced. Additionally, a process may be more or less efficient depending on one or more operating characteristics. There will always be a need for improving process efficiencies and improving equipment reliability.

SUMMARY

The following summary presents a simplified summary of certain features. The summary is not an extensive overview and is not intended to identify key or critical elements.

One or more embodiments may include a system that includes a reactor; a heater; a centrifugal compressor comprising a dry gas seal; one or more sensors associated with the centrifugal compressor; a data collection platform, and/or a data analysis platform. The data collection platform may include one or more processors of the data collection platform; a communication interface of the data collection platform; and computer-readable memory storing executable instructions that, when executed, cause the data collection platform to: receive, from the one or more sensors associated with the centrifugal compressor, sensor data associated with the centrifugal compressor and collected by the one or more sensors associated with the centrifugal compressor; and send the sensor data associated with the centrifugal compressor and collected by the one or more sensors associated with the centrifugal compressor. The data analysis platform may include one or more processors of the data analysis platform; a communication interface of the data analysis platform; and computer-readable memory storing executable instructions that, when executed, cause the data analysis platform to: receive the sensor data associated with the centrifugal compressor and collected by the one or more sensors associated with the centrifugal compressor; analyze the sensor data associated with the centrifugal compressor to determine a composition of gas used in the centrifugal compressor; determine, based on the composition of the gas used in the centrifugal compressor, a potential component failure of the centrifugal compressor; and based on determining the potential component failure of the centrifugal compressor, send a command configured to cause an adjustment to an operating parameter of the centrifugal compressor.

One or more embodiments may include one or more non-transitory computer-readable media storing executable instructions that, when executed, cause a data analysis platform to: receive sensor data associated with a centrifugal compressor and collected by one or more sensors associated with the centrifugal compressor; analyze the sensor data associated with the centrifugal compressor to determine a composition of gas used in the centrifugal compressor; determine, based on the composition of the gas used in the centrifugal compressor, a potential component failure of the centrifugal compressor; and based on determining the potential component failure of the centrifugal compressor, send a command configured to cause an adjustment to an operating parameter of the centrifugal compressor.

One or more embodiments may include a method that includes receiving, by a data analysis computing device, sensor data associated with a centrifugal compressor and collected by one or more sensors associated with the centrifugal compressor; analyzing, by the data analysis computing device, the sensor data associated with the centrifugal compressor to determine a composition of gas used in the centrifugal compressor; determining, by the data analysis computing device and based on the composition of the gas used in the centrifugal compressor, a potential component failure of the centrifugal compressor; and based on determining the potential component failure of the centrifugal compressor, sending, by the data analysis computing device, a command configured to cause an adjustment to an operating parameter of the centrifugal compressor.

Other technical features may be readily apparent to one skilled in the art from the following figures, descriptions, and claims.

BRIEF DESCRIPTION OF DRAWINGS

The present disclosure is illustrated by way of example and not limited in the accompanying figures in which like reference numerals indicate similar elements and in which:

FIGS. 8A and 8B depict an illustrative flow diagram of one or more steps that one more devices may perform in controlling one or more aspects of a plant operation in accordance with one or more example embodiments;

DETAILED DESCRIPTION

In the following description of various illustrative embodiments, reference is made to the accompanying drawings, which form a part hereof, and in which is shown, by way of illustration, various embodiments in which aspects of the disclosure may be practiced. It is to be understood that other embodiments may be used, and structural and functional modifications may be made, without departing from the scope of the present disclosure.

It is noted that various connections between elements are discussed in the following description. It is noted that these connections are general and, unless specified otherwise, may be direct or indirect, wired or wireless, and that the specification is not intended to be limiting in this respect.

A chemical plant or a petrochemical plant or a refinery may include one or more pieces of equipment that process one or more input chemicals to create one or more products. For example, catalytic dehydrogenation can be used to convert paraffins to the corresponding olefin, e.g., propane to propene, or butane to butene.

A multitude of process equipment may be used in the chemical, refining, and petrochemical industry including, but not limited to, slide valves, rotating equipment, pumps, compressors, heat exchangers, fired heaters, control valves, fractionation columns, reactors, and/or shut-off valves.

Elements of chemical and petrochemical/refinery plants may be exposed to the outside and thus can be exposed to various environmental stresses. Such stresses may be weather related, such as temperature extremes (hot and cold), high-wind conditions, and precipitation conditions such as snow, ice, and rain. Other environmental conditions may be pollution particulates, such as dust and pollen, or salt if located near an ocean, for example. Such stresses can affect the performance and lifetime of equipment in the plants. Different locations may have different environmental stresses. For example, a refinery in Texas may have different stresses than a chemical plant in Montana.

Process equipment may deteriorate over time, affecting the performance and integrity of the process. Such deteriorating equipment may ultimately fail, but before failing, may decrease efficiency, yield, and/or product properties. It is desirable that corrective actions be taken in advance of equipment inefficiencies and/or failure.

Figure 1A:
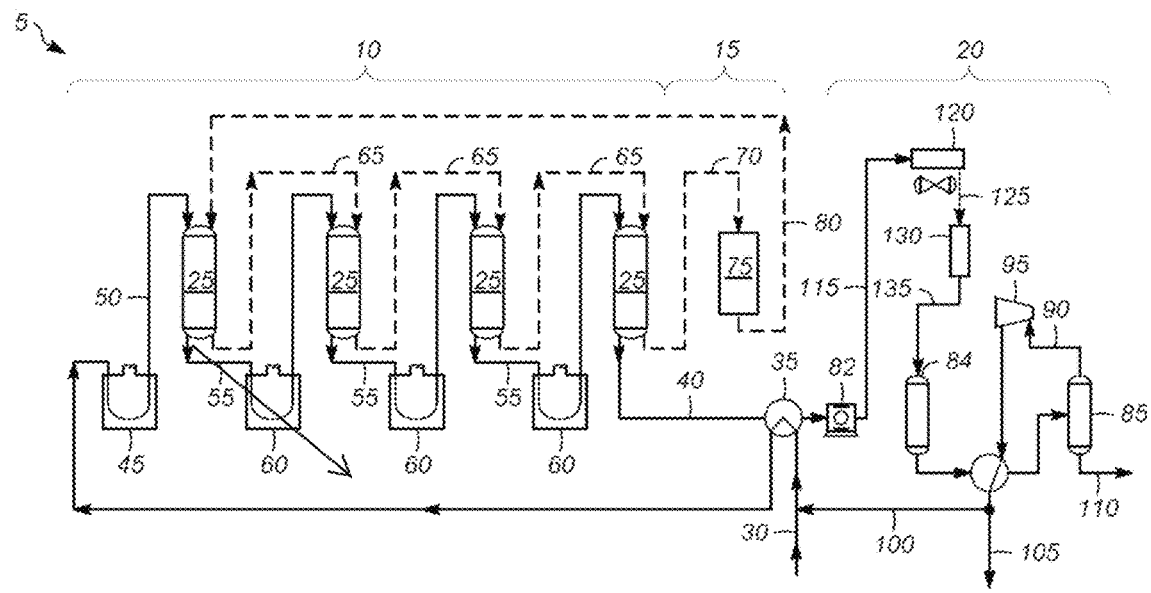
FIG. 1A depicts an illustrative arrangement for a catalytic dehydrogenation process in accordance with one or more example embodiments.

FIG. 1A shows one typical arrangement for a catalytic dehydrogenation process 5. The process 5 includes a reactor section 10, a catalyst regeneration section 15, and a product recovery section 20.

The reactor section 10 includes one or more reactors 25. A hydrocarbon feed 30 is sent to a heat exchanger 35 where it exchanges heat with a reactor effluent 40 to raise the feed temperature. The feed 30 is sent to a preheater 45 where it is heated to the desired inlet temperature. The preheated feed 50 is sent from the preheater 45 to the first reactor 25. Because the dehydrogenation reaction is endothermic, the temperature of the effluent 55 from the first reactor 25 is less than the temperature of the preheated feed 50. The effluent 55 is sent to interstage heaters 60 to raise the temperature to the desired inlet temperature for the next reactor 25.

After the last reactor, the reactor effluent 40 is sent to the heat exchanger 35, and heat is exchanged with the feed 30. The reactor effluent 40 is then sent to the product recovery section 20. The catalyst 65 moves through the series of reactors 25. When the catalyst 70 leaves the last reactor 25, it is sent to the catalyst regeneration section 15. The catalyst regeneration section 15 includes a regenerator 75 where coke on the catalyst is burned off and the catalyst may go through a reconditioning step. A regenerated catalyst 80 is sent back to the first reactor 25.

The reactor effluent 40 is compressed in the compressor or centrifugal compressor 82. The compressed effluent 115 is introduced to a cooler 120, for instance a heat exchanger. The cooler 120 lowers the temperature of the compressed effluent. The cooled effluent 125 (cooled product stream) is then introduced into a chloride remover 130, such as a chloride scavenging guard bed. The chloride remover 130 includes an adsorbent, which adsorbs chlorides from the cooled effluent 125 and provides a treated effluent 135. Treated effluent 135 is introduced to a drier 84.

The dried effluent is separated in separator 85. Gas 90 is expanded in expander 95 and separated into a recycle hydrogen stream 100 and a net separator gas stream 105. A liquid stream 110, which includes the olefin product and unconverted paraffin, is sent for further processing, where the desired olefin product is recovered and the unconverted paraffin is recycled to the dehydrogenation reactor 25.

Figure 1B:
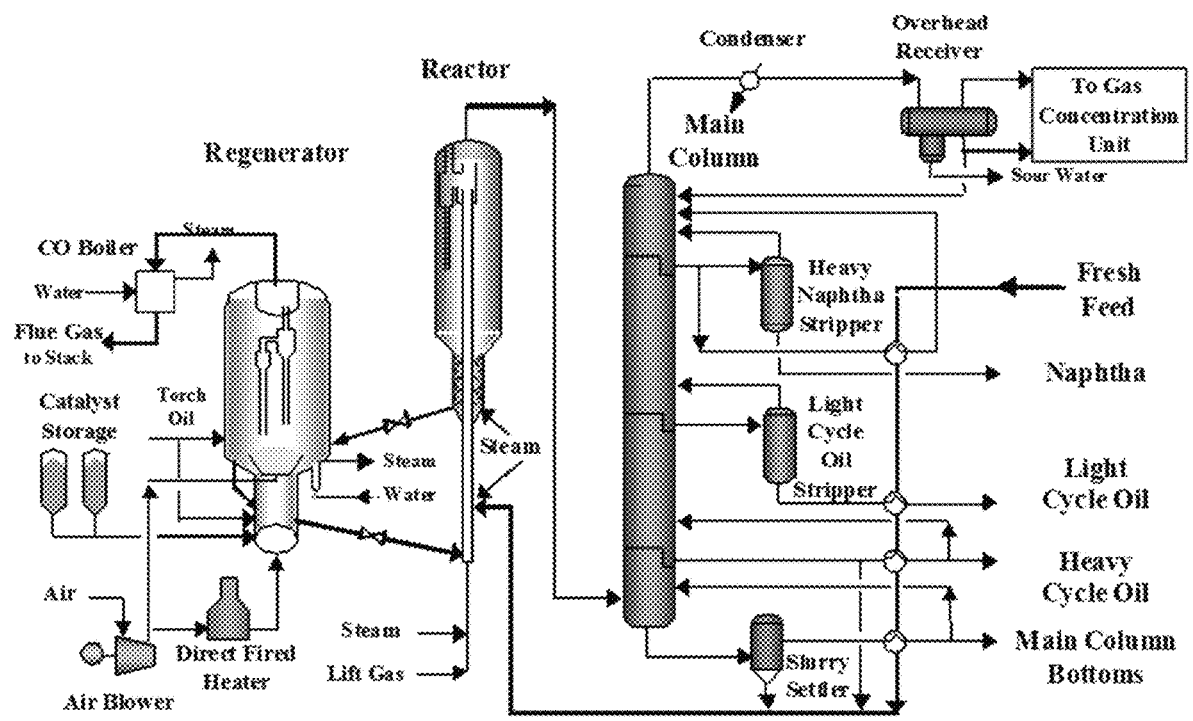
FIG. 1B depicts an illustrative arrangement for a fluid catalytic cracking process in accordance with one or more example embodiments.

FIG. 1B shows a typical fluid catalytic cracking (FCC) process, which includes an FCC fluidized bed reactor and a spent catalyst regenerator. Regenerated cracking catalyst entering the reactor, from the spent catalyst regenerator, is contacted with an FCC feed stream in a riser section at the bottom of the FCC reactor, to catalytically crack the FCC feed stream and provide a product gas stream, comprising cracked hydrocarbons having a reduced molecular weight, on average, relative to the average molecular weight of feed hydrocarbons in the FCC feed stream. As shown in FIG. 1B, steam and lift gas are used as carrier gases that upwardly entrain the regenerated catalyst in the riser section, as it contacts the FCC feed. In this riser section, heat from the catalyst vaporizes the FCC feed stream, and contact between the catalyst and the FCC feed causes cracking of this feed to lower molecular weight hydrocarbons, as both the catalyst and feed are transferred up the riser and into the reactor vessel. A product gas stream comprising the cracked (e.g., lower molecular weight) hydrocarbons may be separated from spent cracking catalyst at or near the top of the reactor vessel, preferably using internal solid/vapor separation equipment, such as cyclone separators. This product gas stream, essentially free of spent cracking catalyst, then exits the reactor vessel through a product outlet line for further transport to the downstream product recovery section.

The spent or coked catalyst, following its disengagement or separation from the product gas stream, requires regeneration for further use. This coked catalyst first falls into a dense bed stripping section of the FCC reactor, into which steam is injected, through a nozzle and distributor, to purge any residual hydrocarbon vapors that would be detrimental to the operation of the regenerator. After this purging or stripping operation, the coked catalyst is fed by gravity to the catalyst regenerator through a spent catalyst standpipe. FIG. 1B depicts a regenerator, which can also be referred to as a combustor. Various configurations of regenerators may be used. In the spent catalyst regenerator, a stream of oxygen-containing gas, such as air, is introduced to contact the coked catalyst, burn coke deposited thereon, and provide regenerated catalyst, having most or all of its initial coke content converted to combustion products, including $CO_2$, CO, and $H_2O$ vapors that exit in a flue gas stream. The regenerator operates with catalyst and the oxygen-containing gas (e.g., air) flowing upwardly together in a combustor riser that is located within the catalyst regenerator. At or near the top of the regenerator, following combustion of the catalyst coke, regenerated cracking catalyst is separated from the flue gas using internal solid/vapor separation equipment (e.g., cyclones) to promote efficient disengagement between the solid and vapor phases.

In the FCC recovery section, the product gas stream exiting the FCC reactor is fed to a bottom section of an FCC main fractionation column. Several product fractions may be separated on the basis of their relative volatilities and recovered from this main fractionation column. Representative product fractions include, for example, naphtha (or FCC gasoline), light cycle oil, and heavy cycle oil.

Other petrochemical processes produce desirable products, such as turbine fuel, diesel fuel and other products referred to as middle distillates, as well as lower boiling hydrocarbonaceous liquids, such as naphtha and gasoline, by hydrocracking a hydrocarbon feedstock derived from crude oil or heavy fractions thereof. Feedstocks most often subjected to hydrocracking are the gas oils and heavy gas oils recovered from crude oil by distillation.

References herein to a "plant" are to be understood to refer to any of various types of chemical and petrochemical manufacturing or refining facilities. References herein to a plant "operators" are to be understood to refer to and/or include, without limitation, plant planners, managers, engineers, technicians, operators, and others interested in, overseeing, and/or running the daily operations at a plant.

Rotating Equipment Technology

A system or arrangement as described above may include various compressors, pumps, and/or turbines, and FIGS. 1A and 1B illustrate example locations for some of such components, which may be additionally or alternately used in other locations. Compressors may be used to compress gases within the system (e.g., a reactor effluent) to provide a compressed gas. Compression includes increasing a pressure of the gas and may also change other properties such as temperature. Pumps may be used to force fluids through the system. Centrifugal pumps are an example of a frequently used pump in a plant as described herein. Turbines may be used for harnessing heat energy generated by the plant, such as to convert the heat energy into electrical energy and/or to power fans or other rotating equipment. Steam turbines, for example, are often used in a plant as described herein.

Figure 2:
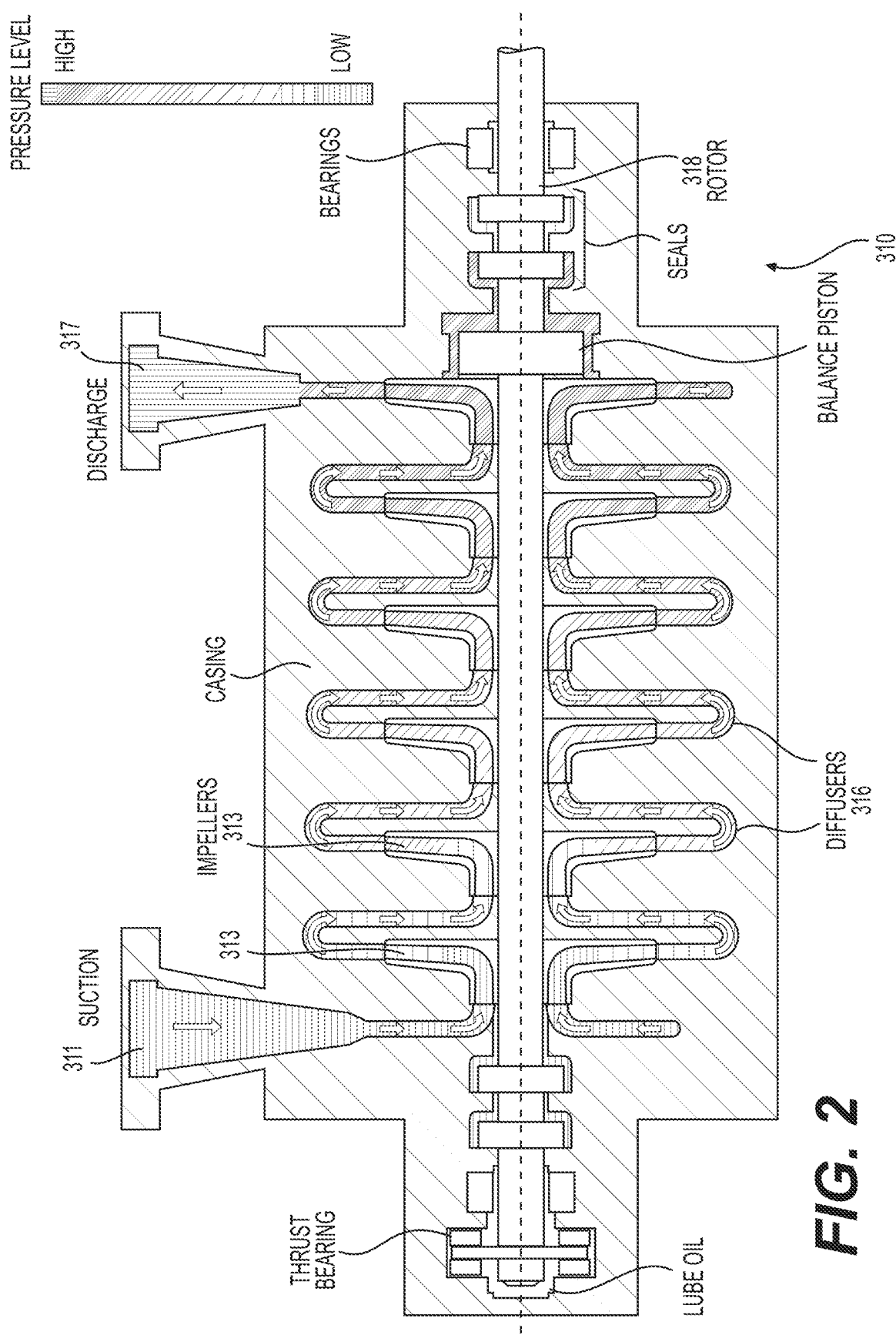
FIG. 2 depicts an illustrative arrangement for a centrifugal compressor configured for use in connection with the arrangement of FIGS. 1A and/or 1B in accordance with one or more example embodiments.
Figure 3:
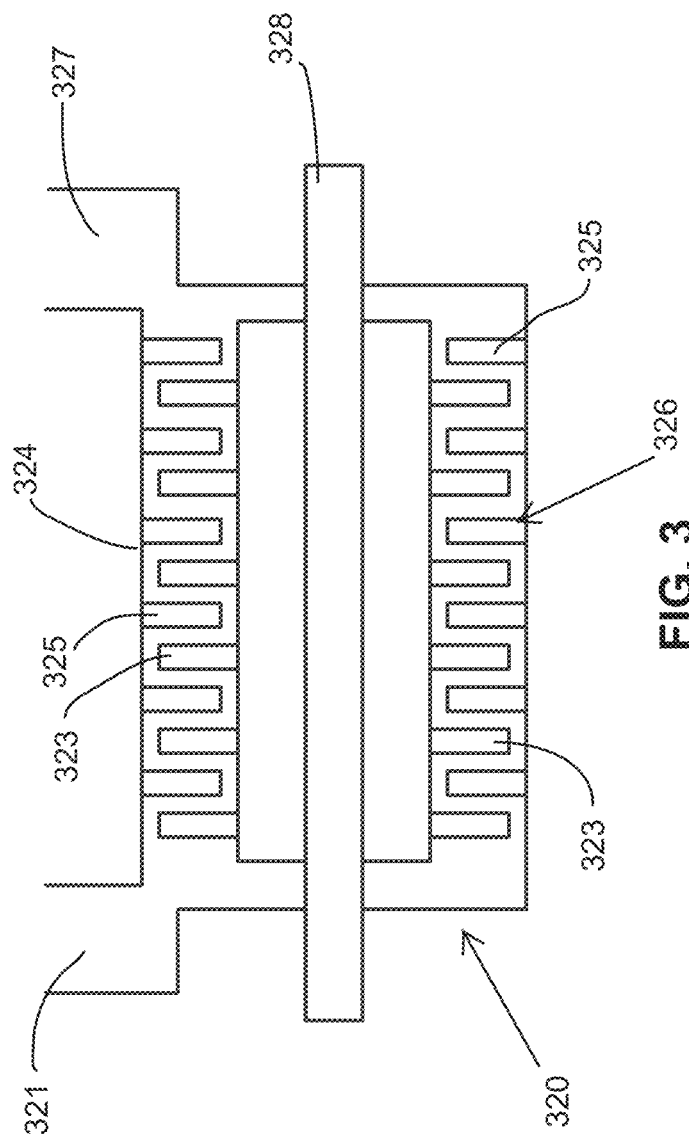
FIG. 3 depicts an illustrative arrangement for an axial compressor configured for use in connection with the arrangement of FIGS. 1A and/or 1B in accordance with one or more example embodiments.

There are several types of compressors typically used in chemical and petrochemical plants and refineries, the most common of which are centrifugal compressors, axial compressors, and reciprocating compressors. Many compressors in a plant as described herein are arranged in parallel with a redundant backup compressor, which can be activated to prevent total shutdown when the original compressor needs to be taken offline. Centrifugal and axial compressors are dynamic compressors that operate by transferring energy from a set of rotating impeller blades to a gas, which is then converted into potential energy in the form of increased gas pressure by diffusers that slow the flow of the gas, creating a pressurized output gas. FIG. 2 illustrates an example of a centrifugal compressor 310, which includes an inlet or intake 311, a plurality of impellers 313 mounted on a rotatable shaft 318 and located downstream from the inlet 311, and a plurality of diffusers 316 each located following one of the impellers 313, and an outlet or discharge 317 at the far downstream end of the compressor 310. The compressor 310 operates by building pressure incrementally and sequentially in the diffusers 316. FIG. 3 illustrates an example of an axial compressor 320, which includes an inlet or intake 321 a plurality of impellers 323 mounted on a rotatable shaft 328 and located downstream from the inlet 321, a stator 324 that has a plurality of stator vanes 325 arranged in circumferential rings each located downstream from one of the impellers 323 and operates as a diffuser 326, and an outlet or discharge 327 at the far downstream end of the compressor 320.

Centrifugal or axial compressors may be referred to as dynamic compressors or turbomachinery. Such compressors often have other components immediately upstream and downstream that enhance or enable the functioning of the compressor. Examples of such equipment include isolation valves, a suction strainers, a compressor suction drum or separator, an anti-surge spillback takeoff, a feed mix node and combined feed exchanger for $H_2$ recycle, and an interstage drum or knockout drum.

Performance of all types of compressors may be affected by changes in gas conditions, including gas temperature and the composition and/or molecular weight of the gas, among other factors. Process control of capacity may be made by speed variation, suction throttling, or variable inlet guide vanes. Compressors can be put through a variety of extreme conditions, such as high temperatures and pressures and corrosive and aggressive components.

Surge is a common issue faced by all centrifugal and axial compressors. Surge occurs when the outlet or discharge pressure of the compressor is equal to or greater than the pressure generated by the impellers 313, 323. In a centrifugal or axial compressor, this phenomenon typically occurs within the final diffuser 316, 326 before the outlet 317, 327. When this occurs, the increased outlet pressure drives airflow temporarily backward toward the impeller or impellers 313, 323. Surge typically happens in an oscillatory manner and is often accompanied by rapid (even exponential) temperature increase. Various factors can cause surging, such as increased discharge pressure, improper valve cycling, change in gas composition (e.g., decreased molecular weight of the gas), ramping the feed rate too fast, improper limit stop set point on the valves, and other operational errors or malfunctions, among other factors. Surge can decrease the effectiveness and efficiency of the compressor, and the vibrations, thrust reversals, and temperature increases that result from surging can damage components of the compressor (sometimes quickly) and reduce the functional life of the compressor. For example, vibrations and thrust reversal can cause damage to bearings and seals, and potentially cause contact between rotating and stationary parts. As another example, temperature increases can cause damage to seals, thermal expansion of the rotor/impeller, and contact between rotating and stationary parts.

Figure 4:
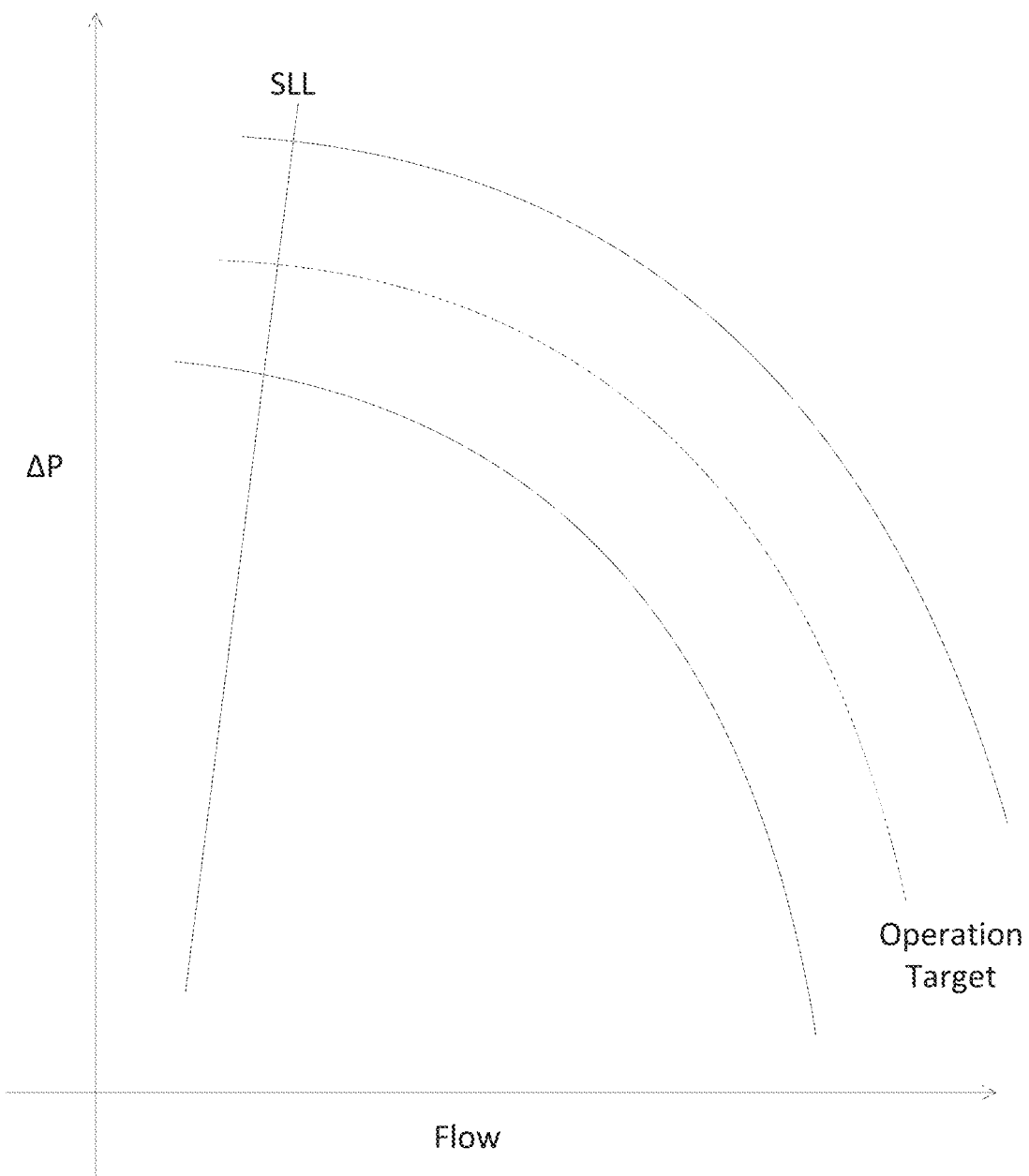
FIG. 4 depicts a graph illustrating typical performance operation of a centrifugal or axial compressor in accordance with one or more example embodiments.

Each dynamic compressor has a surge limit that represents a limit on operation of the compressor. FIG. 4 illustrates the performance operating of a centrifugal compressor, plotting change in pressure ($\Delta P$) against flow, with the surge limit forming a performance limitation of the compressor. Normal operation occurs between the lines defined by the maximum and minimum compressor speeds and to the right of the surge line, and surge occurs when the surge line is crossed. An axial compressor may perform in a similar manner.

Additional issues faced by centrifugal or axial compressors include bearing and seal failures, wear, fouling, and damage from contact between moving and non-moving components, among others. Such failures may be caused by vibrations, thrust reversals, excessive temperature, and unwanted chemicals in the feed gas. Some of these issues may directly or indirectly result from surging, but these issues may result from other causes as well, including other causes described elsewhere herein.

Figure 5A:
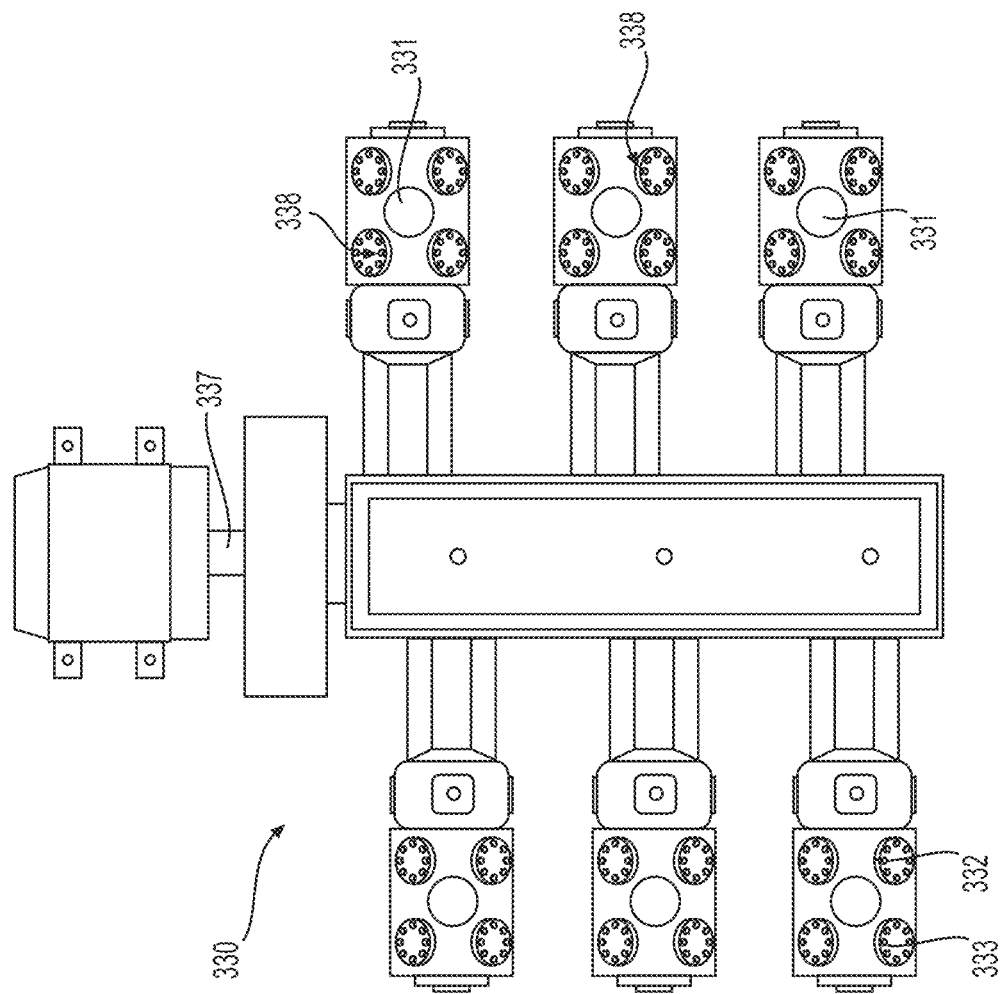
FIG. 5A depicts an illustrative arrangement for a portion of a reciprocating compressor configured for use in connection with the arrangement of FIGS. 1A and/or 1B in accordance with one or more example embodiments.
Figure 5B:
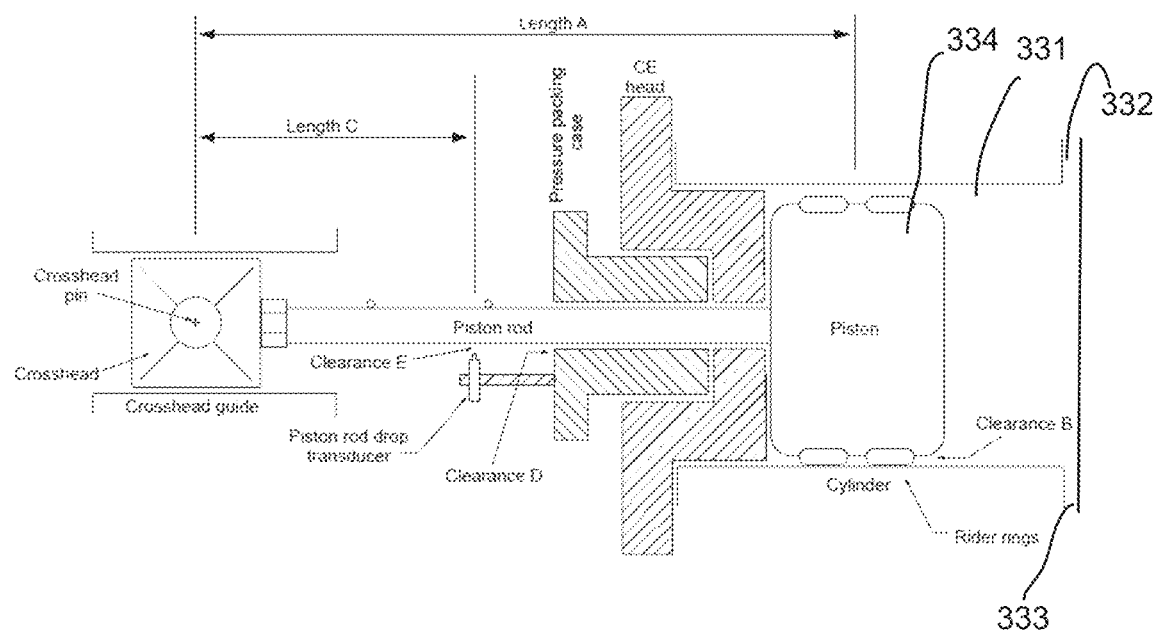
FIG. 5B depicts an illustrative arrangement for a reciprocating compressor configured for use in connection with the arrangement of FIGS. 1A and/or 1B in accordance with one or more example embodiments.

A reciprocating compressor is a positive-displacement compressor that operates by a moveable member, e.g., a piston and/or a membrane/diaphragm, moving to decrease the volume of a cylinder filled with a gas, thereby compressing the gas within the cylinder. FIG. 5A illustrates an example of a piston-type reciprocating compressor 330, which includes a cylinder 331 with an inlet or intake 332 and an outlet or discharge 333, with a piston 334 that reciprocates to draw gases in through the inlet 332 and compress gases contained in the cylinder 331. The inlet 332 and the outlet 333 may further have inlet and outlet valves to permit intake of gas through the inlet 332 and discharge of compressed gas through the outlet 333 at appropriate times. The opening and closing of such valves is critical to the operation of the compressor. The valves should operate smoothly and timely as well as fully open and close at appropriate times. Vibrations and contaminants can affect the performance and integrity of the valves and their operation The compressor 330 illustrated in FIG. 5B also includes a piston rod, a crosshead connected to the piston rod that rides within a crosshead guide, a crosshead pin, rider rings on the piston 334, a head end or cylinder end (CE) head, a pressure packing case, and a piston rod drop transducer. Many reciprocating compressors may include multiple cylinders 331 as shown in FIG. 5A, and the inlets in such an embodiment may be provided through an intake manifold or suction manifold. FIG. 5A also illustrates the valve heads 338 of the compressor 330. The piston(s) 334 in a reciprocating compressor 330 may be driven by a crankshaft 337 in one or more embodiments.

Reciprocating compressors often have other components immediately upstream and downstream that enhance or enable the functioning of the compressor. Examples of such equipment include an isolation valve, a suction strainer, an interstage cooler or aftercooler, and a discharge drum.

One issue facing reciprocating compressors is ingress of liquid contaminants, which may occur through a variety of mechanisms, such as improper separation between gas and liquid components at some point along the line, seal leakage, condensation caused by insufficient temperature at some point along the line and compounded by poor suction pipe layout. Liquids are incompressible, and therefore, ingress of liquids into the compressor can negatively affect operation of the compressor. Other contaminants, such as particulates or debris entrained in the gas flow, also present issues for reciprocating compressors. Ingress of liquid or other contaminants can damage a reciprocating compressor, and in particular may cause valve distress and failure. Ingress of such contaminants may also cause fouling of equipment, process drifting, and/or decreasing capacity and efficiency.

Figure 6:
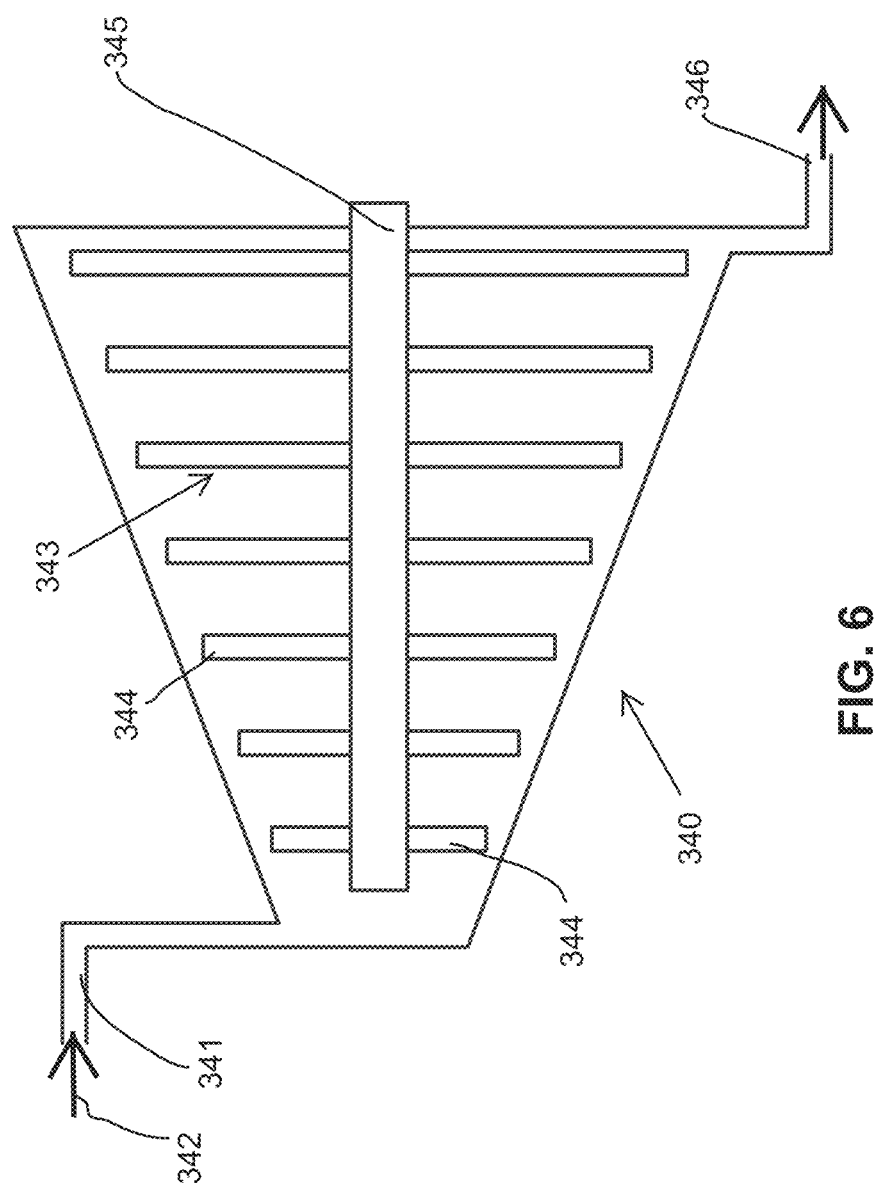
FIG. 6 depicts an illustrative arrangement for a steam turbine configured for use in connection with the arrangement of FIGS. 1A and/or 1B in accordance with one or more example embodiments.

A turbine is a device that extracts energy from a fluid flow and converts it into work, e.g., mechanical or electrical power. FIG. 6 illustrates an example of a steam turbine 340 that may be used in a plant as described herein. The turbine 340 includes an inlet 341 that receives steam 342 from a steam source, a rotor 343 with blades 344 that are acted on by the impulse of the steam 342 flowing through the inlet 341 to turn the rotor 343, and a shaft 345 that is rotated by the rotor 343 to generate mechanical power (e.g., by connection to gears) or electrical power (e.g., by use of induction equipment). The steam then escapes through an outlet 346. Heat generated by various components of the plant may be harnessed to create steam at the steam source, which is passed to the steam turbine 340 for conversion to mechanical or electrical power.

Issues faced by turbines in petrochemical plants include failure of trip and throttle valves, damage to flow path components (e.g., stationary or rotating blades) due to "wet" steam that is not of sufficiently high temperature, and failure of the turbine for mechanical reasons.

In various embodiments described herein, as described in further detail below, different types of sensors may be used in and around rotating equipment components such as compressors and turbines, including centrifugal compressors, axial compressors, reciprocating compressors, and/or steam turbines as described above. Data from such sensors can then be analyzed in a manual and/or automated manner, and corrective actions or recommendations for such actions can be generated based on such analysis. It is understood that any sensor described herein may be configured for communicating the data gathered by the sensor to a computer system, including by various wired or wireless technologies. In one or more embodiments, each sensor described herein may include a wireless transmitter (or transceiver) for wirelessly communicating with a computer system. In another embodiment, some or all of the sensors described herein may include an individual processor and/or memory configured for processing communications to/from the computer system or processing and/or storing data independently or in conjunction with the computer system.

Sensor Data Collection and Processing

Figure 7A:
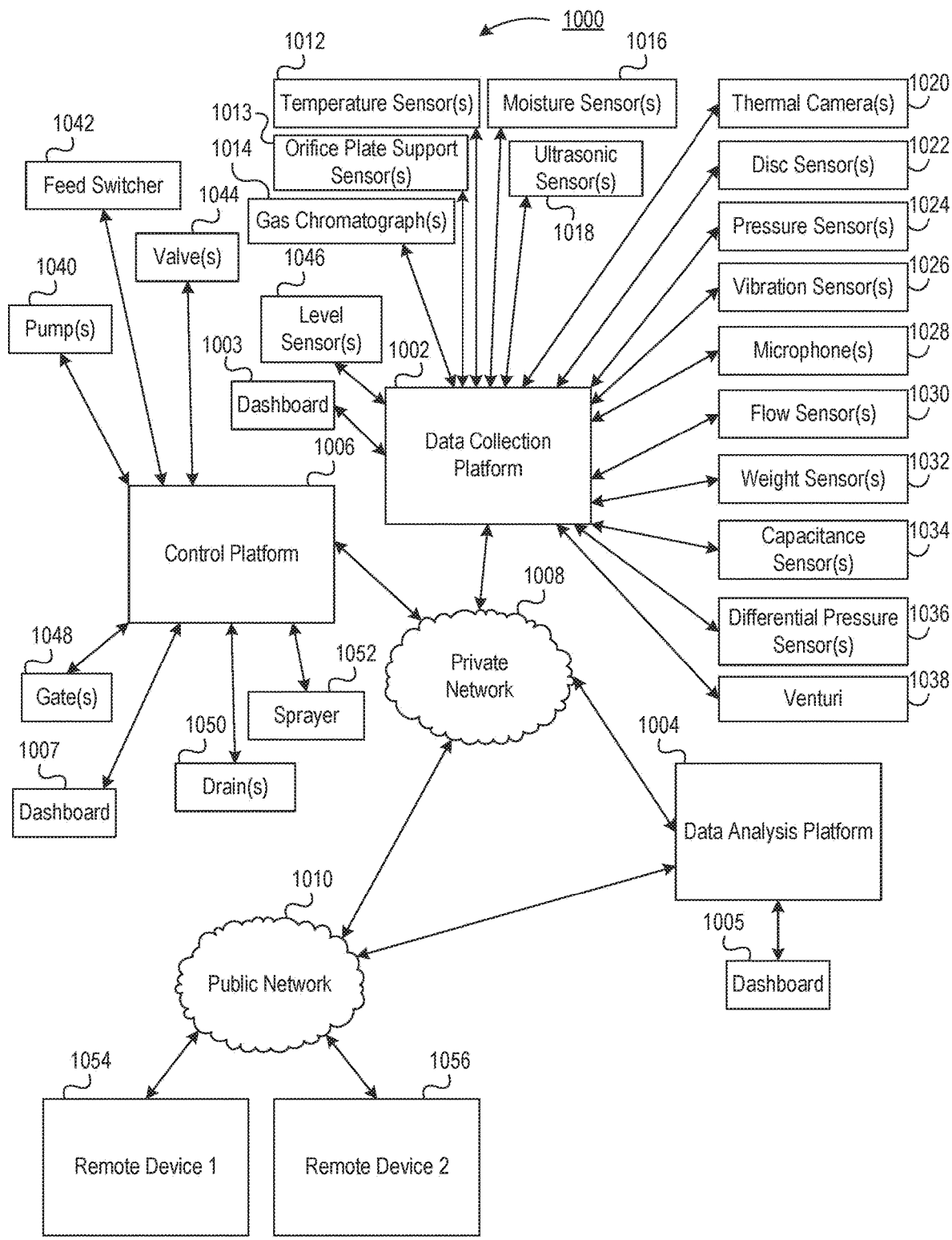
FIG. 7A depicts an illustrative computing environment for managing the operation of one or more pieces of equipment in a plant in accordance with one or more example embodiments.

The system may include one or more computing devices or platforms for collecting, storing, processing, and analyzing data from one or more sensors. FIG. 7A depicts an illustrative computing system that may be implemented at one or more components, pieces of equipment (e.g., rotating equipment), and/or plants. FIG. 7A-FIG. 7E, show, by way of illustration, various components of the illustrative computing system in which aspects of the disclosure may be practiced. It is to be understood that other components may be used, and structural and functional modifications may be made, in one or more other embodiments without departing from the scope of the present disclosure. Moreover, various connections between elements are discussed in the following description, and these connections are general and, unless specified otherwise, may be direct or indirect, wired or wireless, and/or combination thereof, and that the specification is not intended to be limiting in this respect.

FIG. 7A depicts an illustrative operating environment in which various aspects of the present disclosure may be implemented in accordance with example embodiments. The computing system environment 1000 illustrated in FIG. 7A is only one example of a suitable computing environment and is not intended to suggest any limitation as to the scope of use or functionality contained in the disclosure. The computing system environment 1000 may include various sensor, measurement, and data capture systems, a data collection platform 1002, a data analysis platform 1004, a control platform 1006, one or more networks, one or more remote devices 1054, 1056, and/or one or more other elements. The numerous elements of the computing system environment of FIG. 7A may be communicatively coupled through one or more networks. For example, the numerous platforms, devices, sensors, and/or components of the computing system environment may be communicatively coupled through a private network 1008. The sensors be positioned on various components in the plant and may communicate wirelessly or wired with one or more platforms illustrated in FIG. 7A. The private network 1008 may include, in some examples, a network firewall device to prevent unauthorized access to the data and devices on the private network 1008. Alternatively or additionally, the private network 1008 may be isolated from external access through physical means, such as a hard-wired network with no external, direct access point. The data communicated on the private network 1008 may be optionally encrypted for further security. Depending on the frequency of collection and transmission of sensor measurements and other data to the data collection platform 1002, the private network 1008 may experience large bandwidth usage and be technologically designed and arranged to accommodate for such technological issues. Moreover, the computing system environment 1000 may also include a public network 1010 that may be accessible to remote devices (e.g., remote device 1054, remote device 1056). In some examples, a remote device may be located not in the proximity (e.g., more than one mile away) of the various sensor, measurement, and data capture systems illustrated in FIG. 7A. In other examples, the remote device may be physically located inside a plant, but restricted from access to the private network 1008; in other words, the adjective "remote," need not necessarily require the device to be located at a great distance from the sensor systems and other components.

Although the computing system environment of FIG. 7A illustrates logical block diagrams of numerous platforms and devices, the disclosure is not so limited. In particular, one or more of the logical boxes in FIGS. 7A to 7E may be combined into a single logical box or the functionality performed by a single logical box may be divided across multiple existing or new logical boxes. For example, aspects of the functionality performed by the data collection platform 1002 may be incorporated into one or each of the sensor devices illustrated in FIG. 7A. As such, the data collection may occur local to the sensor device, and the enhanced sensor system may communicate directly with one or more of the control platform 1006 and/or data analysis platform 1004. An illustrative example of such an embodiment is contemplated by FIG. 7A. Moreover, in such an embodiment, the enhanced sensor system may measure values common to a sensor, but may also filter the measurements such just those values that are statistically relevant or of-interest to the computing system environment are transmitted by the enhanced sensor system. As a result, the enhanced sensor system may include a processor (or other circuitry that enables execution of computer instructions) and a memory to store those instructions and/or filtered data values. The processor may be embodied as an application-specific integrated circuit (ASIC), FPGA, or other hardware- or software-based module for execution of instructions. In another example, one or more sensors illustrated in FIG. 7A may be combined into an enhanced, multi-purpose sensor system. Such a combined sensor system may provide economies of scale with respect to hardware components such as processors, memories, communication interfaces, and others.

In yet another example, the data collection platform 1002 and data analysis platform 1004 may reside on a single server computer and depicted as a single, combined logical box on a system diagram. Moreover, a data store may be illustrated in FIG. 7A separate and apart from the data collection platform 1002 and data analysis platform 1004 to store a large amount of values collected from sensors and other components. The data store may be embodied in a database format and may be made accessible to the public network 1010; meanwhile, the control platform 1006, data collection platform 1002, and data analysis platform 1004 may be restricted to the private network 1008 and left inaccessible to the public network 1010. As such, the data collected from a plant may be shared with users (e.g., engineers, data scientists, others), a company's employees, and even third parties (e.g., subscribers to the company's data feed) without compromising potential security requirements related to operation of a plant. The data store may be accessible to one or more users and/or remote devices over the public network 1010.

Referring to FIG. 7A, process measurements from various sensor and monitoring devices may be used to monitor conditions in, around, and on process equipment (e.g., rotating equipment). Such sensors may include, but are not limited to, pressure sensors 1024, differential pressure sensors 1036, various flow sensors (including but not limited to orifice plate type 1013, disc sensors 1022, venturi 1038, other flow sensors 1030), temperature sensors 1012 including thermal cameras 1020 and skin thermocouples, capacitance sensors 1034, weight sensors 1032, gas chromatographs 1014, moisture sensors 1016, ultrasonic sensors 1018, position sensors, timing sensors, vibration sensors 1026, microphones 1028, level sensors 1046, liquid level (hydraulic fluid) sensors, and other sensors used in the refining and petrochemical industry. Further, process laboratory measurements may be taken using gas chromatographs 1014, liquid chromatographs, distillation measurements, octane measurements, and other laboratory measurements. System operational measurements also can be taken to correlate the system operation to the rotating equipment measurements.

In addition, sensors may include transmitters and/or deviation alarms. One or more sensors may be programmed to set off an alarm or alert. For example, if an actuator fails, sensor data may be used to automatically trigger an alarm or alert (e.g., an audible alarm or alert, a visual alarm or alert). Other sensors may transmit signals to a processor or a hub that collects the data and sends to a processor. For example, temperature and pressure measurements may be sent to a hub (e.g., data collection platform 1002). In one or more embodiments, temperature sensors 1012 may include thermocouples, fiber optic temperature measurement, thermal cameras 1020, and/or infrared cameras. Skin thermocouples may be applied to rotating equipment casing, or alternatively, to tubes, plates, or placed directly on a wall of a rotating equipment component. Alternatively, thermal (infrared) cameras 1020 may be used to detect temperature in one or more aspects of the equipment. A shielded (insulated) tube skin thermocouple assembly may be used to obtain accurate measurements. One example of a thermocouple may be a removable Xtracto™ Pad. A thermocouple can be replaced without any additional welding. Clips and/or pads may be used for ease of replacement. Fiber Optic cable can be attached to the pipe, line, and/or vessel to provide a complete profile of temperatures.

Sensors may be also used throughout a plant or rotating equipment to detect and monitor various issues such as PV detection, surge detection, fouling, gas quality, dew point characteristics, and/or production levels. Sensors might be able to detect whether feed composition into the rotating equipment, such as pH, are outside of acceptable ranges leading to a corrosive environment or whether consumption of sacrificial anodes (in water services) is nearing completion and resulting in a corrosive environment. Sensors detecting outlet temperatures and pressure drops may be used to determine/predict flow and production rate changes.

Furthermore, flow sensors may be used in flow paths such as the inlet to the path, outlet from the path, or within the path. If multiple tubes are used, the flow sensors may be placed in corresponding positions in each of the rotating machines. In this manner, one can determine if one of the rotating machines is behaving abnormally compared to one or more others. Flow may be determined by pressure-drop across a known resistance, such as by using pressure taps. In other examples, flow may be inferred using fluid density in addition to suction and discharge pressures. Other types of flow sensors include, but are not limited to, ultrasonic, turbine meter, hot wire anemometer, vane meter, Kármán™, vortex sensor, membrane sensor (membrane has a thin film temperature sensor printed on the upstream side, and one on the downstream side), tracer, radiographic imaging (e.g. identify two-phase vs. single-phase region of channels), an orifice plate (e.g., which may in some examples, be placed in front of one or more tube or channels), pitot tube, thermal conductivity flow meter, anemometer, internal pressure flow profile.

Sensor data, process measurements, and/or calculations made using the sensor data or process measurements may be used to monitor and/or improve the performance of the equipment and parts making up the equipment, as discussed in further detail below. For example, sensor data may be used to detect that a desirable or an undesirable chemical reaction is taking place within a particular piece of equipment, and one or more actions may be taken to encourage or inhibit the chemical reaction. Chemical sensors may be used to detect the presence of one or more chemicals or components in the streams, such as corrosive species, oxygen, hydrogen, and/or water (moisture). Chemical sensors may use gas chromatographs, liquid chromatographs, distillation measurements, and/or octane measurements. In another example, equipment information, such as wear, efficiency, production, state, or other condition information, may be gathered and determined based on sensor data. Corrective action may be taken based on determining this equipment information. For example, if the equipment is showing signs of wear or failure, corrective actions may be taken, such as taking an inventory of parts to ensure replacement parts are available, ordering replacement parts, and/or calling in repair personnel to the site. Certain parts of equipment may be replaced immediately. Other parts may be safe to use, but a monitoring schedule may be adjusted. Alternatively or additionally, one or more inputs or controls relating to a process may be adjusted as part of the corrective action. These and other details about the equipment, sensors, processing of sensor data, and actions taken based on sensor data are described in further detail below.

Monitoring the rotating equipment and the processes using rotating equipment includes collecting data that can be correlated and used to predict behavior or problems in different rotating equipment used in the same plant or in other plants and/or processes. Data collected from the various sensors (e.g., measurements such as flow, pressure drop, thermal performance, vessel skin temperature at the top, expansion bellows leak, vibration, etc.) may be correlated with external data, such as environmental or weather data. Process changes or operating conditions may be able to be altered to preserve the equipment until the next scheduled maintenance period. Fluids may be monitored for corrosive contaminants and pH may monitored in order to predict higher than normal corrosion rates within the rotating equipment.

Systems Facilitating Sensor Data Collection

Sensor data may be collected by a data collection platform 1002. The sensors may interface with the data collection platform 1002 via wired or wireless transmissions. The data collection platform 1002 may continuously or periodically (e.g., every second, every minute, every hour, every day, once a week, once a month) transmit collected sensor data to a data analysis platform 1004, which may be nearby or remote from the data collection platform 1002.

Sensor data (e.g., temperature data) may be collected continuously or at periodic intervals (e.g., every second, every five seconds, every ten seconds, every minute, every five minutes, every ten minutes, every hour, every two hours, every five hours, every twelve hours, every day, every other day, every week, every other week, every month, every other month, every six months, every year, or another interval). Data may be collected at different locations at different intervals. For example, data at a known hot spot may be collected at a first interval, and data at a spot that is not a known hot spot may be collected at a second interval. The data collection platform transmit collected sensor data to a data analysis platform, which may be nearby or remote from the data collection platform.

Figure 7B:
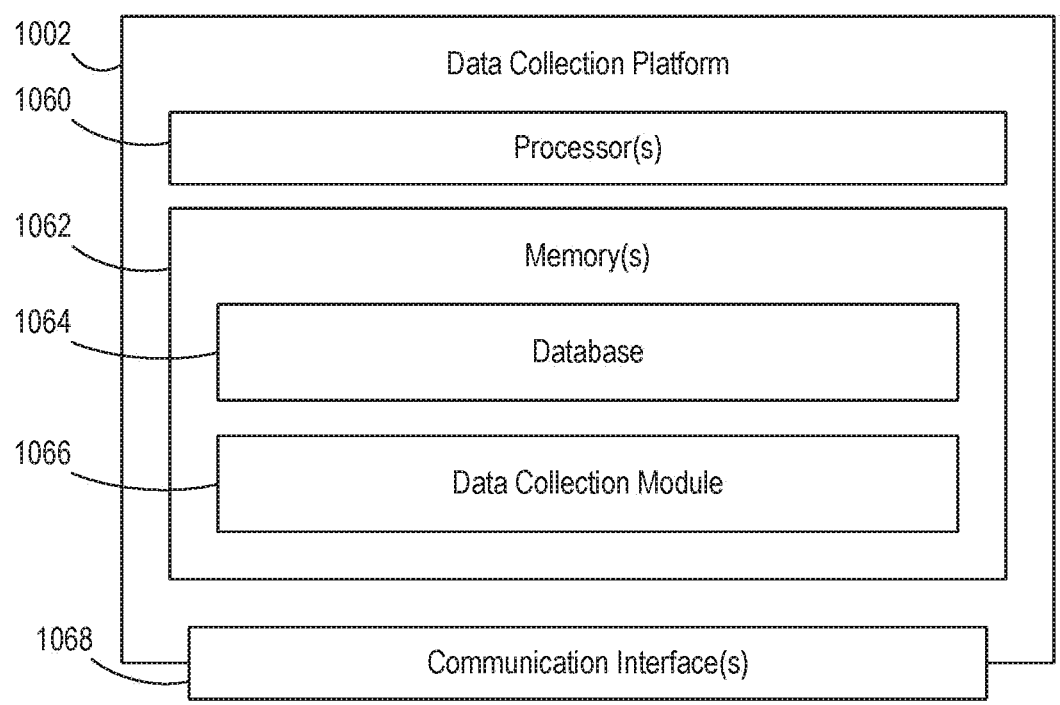
FIG. 7B depicts an illustrative data collection computing platform for collecting data related to the operation of one or more pieces of equipment in a plant in accordance with one or more example embodiments.
Figure 7C:
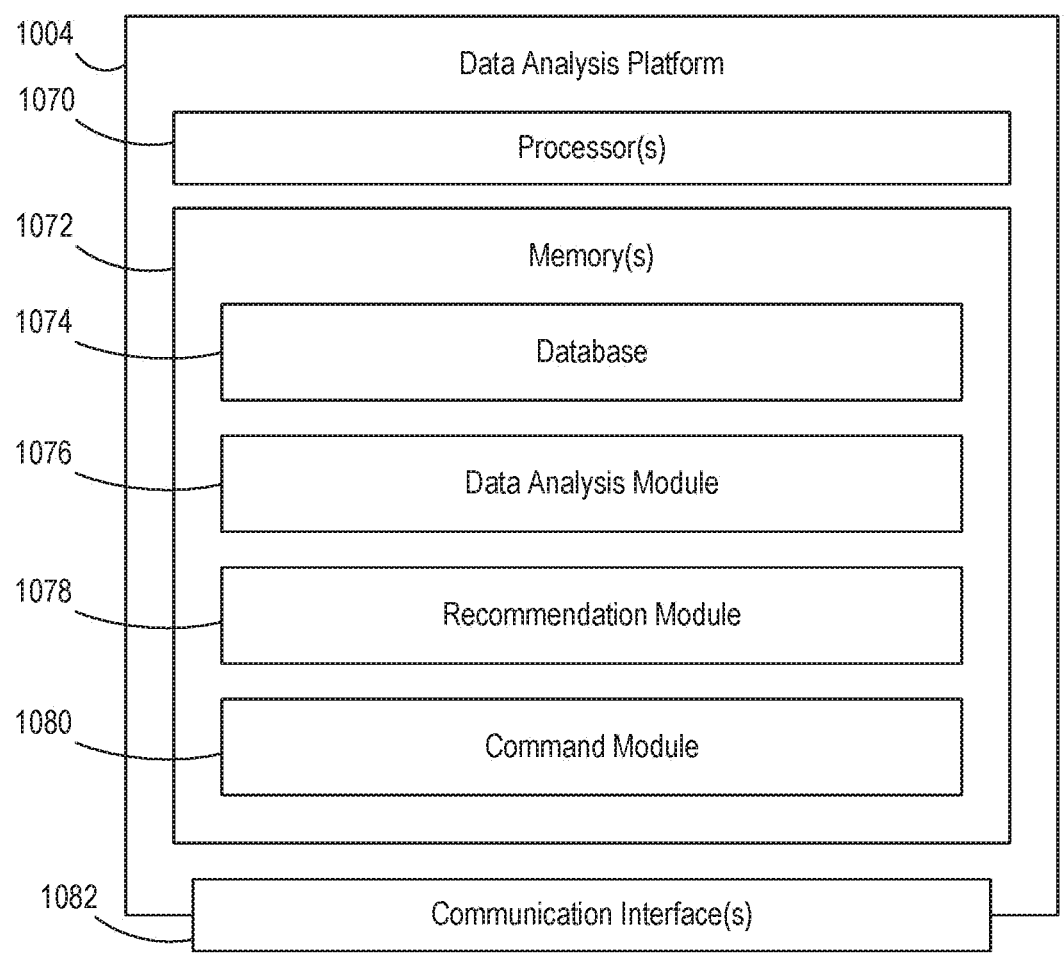
FIG. 7C depicts an illustrative data analysis computing platform for analyzing data related to the operation of one or more pieces of equipment in a plant in accordance with one or more example embodiments.
Figure 7D:
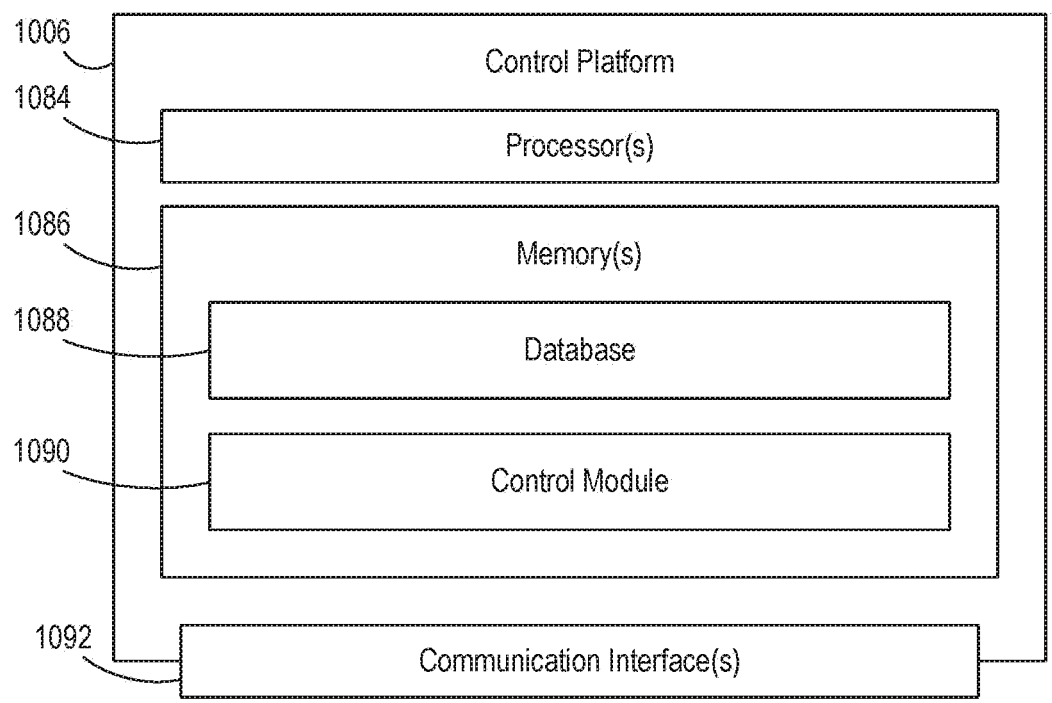
FIG. 7D depicts an illustrative data analysis computing platform for analyzing data related to the operation of one or more pieces of equipment in a plant in accordance with one or more example embodiments.
Figure 7E:
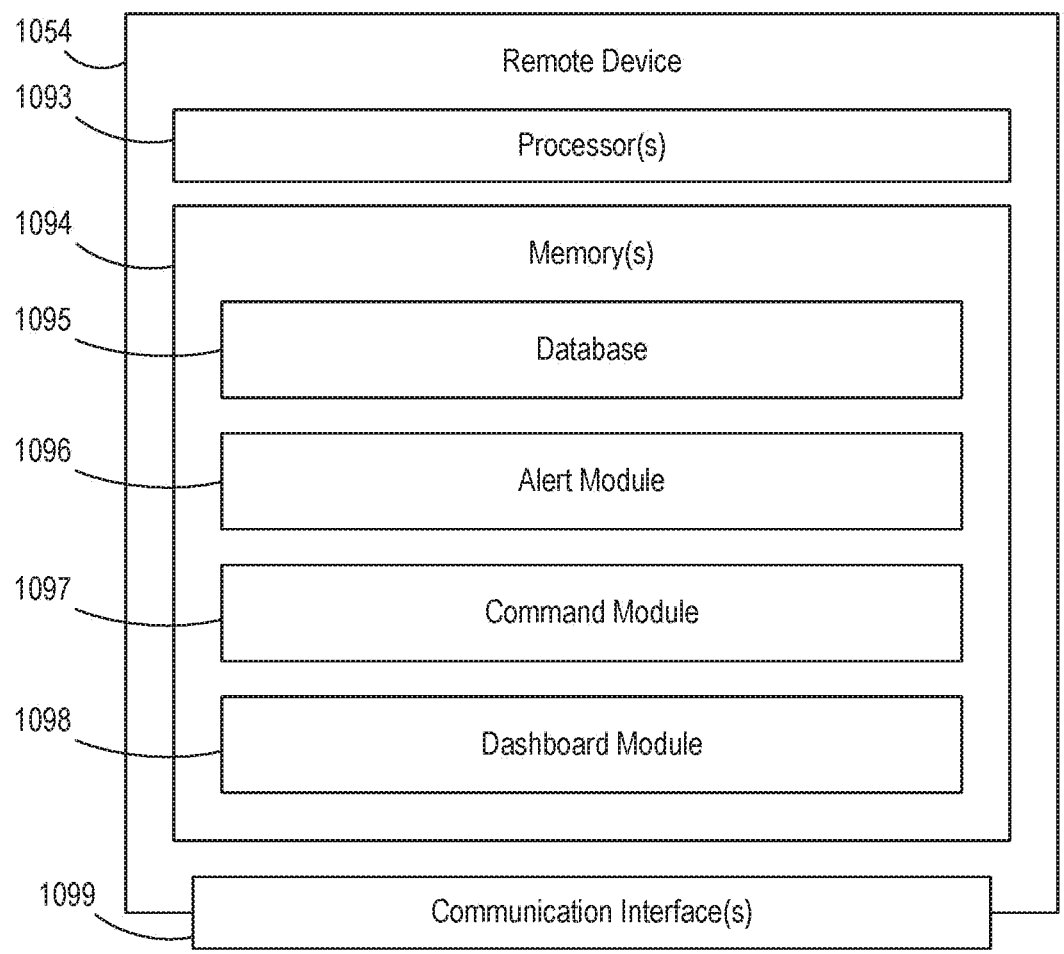
FIG. 7E depicts an illustrative control computing platform for controlling one or more parts of one or more pieces of equipment in a plant in accordance with one or more example embodiments.

The computing system environment of FIG. 7A includes logical block diagrams of numerous platforms and devices that are further elaborated upon in FIG. 7B, FIG. 7C, FIG. 7D, and FIG. 7E. FIG. 7B is an illustrative data collection platform 1002. FIG. 7C is an illustrative data analysis platform 1004. FIG. 7D is an illustrative control platform 1006. FIG. 7E is an illustrative remote device 1054. These platforms and devices of FIGS. 7A to 7E include one or more processing units (e.g., processors) to implement the methods and functions of certain aspects of the present disclosure in accordance with the example embodiments. The processors may include general-purpose microprocessors and/or special-purpose processors designed for particular computing system environments or configurations. For example, the processors may execute computer-executable instructions in the form of software and/or firmware stored in the memory of the platform or device. Examples of computing systems, environments, and/or configurations that may be suitable for use with the disclosed embodiments include, but are not limited to, personal computers (PCs), server computers, hand-held or laptop devices, smart phones, multiprocessor systems, microprocessor-based systems, programmable consumer electronics, network PCs, minicomputers, mainframe computers, distributed computing environments that include any of the above systems or devices, and the like.

In addition, the platform and/or devices in FIGS. 7A to 7E may include one or more memories include any of a variety of computer readable media. Computer-readable media may be any available media that may be accessed by the data collection platform 1002, may be non-transitory, and may include volatile and nonvolatile, removable and non-removable media implemented in any method or technology for storage of information such as computer-readable instructions, object code, data structures, database records, program modules, or other data. Examples of computer-readable media may include random access memory (RAM), read only memory (ROM), electronically erasable programmable read only memory (EEPROM), flash memory or other memory technology, compact disk read-only memory (CD-ROM), digital versatile disks (DVD) or other optical disk storage, magnetic cassettes, magnetic tape, magnetic disk storage or other magnetic storage devices, or any other medium that can be used to store the desired information and that can be accessed by the data collection platform 1002. The memories in the platform and/or devices may further store modules that may include compiled software code that causes the platform, device, and/or overall system to operate in a technologically improved manner as disclosed herein. For example, the memories may store software used by a computing platform, such as operating system, application programs, and/or associated database.

Furthermore, the platform and/or devices in FIGS. 7A to 7E may include one or more communication interfaces including, but are not limited to, a microphone, keypad, keyboard, touch screen, and/or stylus through which a user of a computer (e.g., a remote device) may provide input, and may also include a speaker for providing audio output and a video display device for providing textual, audiovisual and/or graphical output. Input may be received via one or more graphical user interfaces, which may be part of one or more dashboards (e.g., dashboard 1003, dashboard 1005, dashboard 1007). The communication interfaces may include a network controller for electronically communicating (e.g., wirelessly or wired) over a public network 1010 or private network 1008 with one or more other components on the network. The network controller may include electronic hardware for communicating over network protocols, including TCP/IP, UDP, Ethernet, and other protocols.

In some examples, one or more sensor devices in FIG. 7A may be enhanced by incorporating functionality that may otherwise be found in a data collection platform 1002. These enhanced sensor system may provide further filtering of the measurements and readings collected from their sensor devices. For example, with some of the enhanced sensor systems in the operating environment illustrated in FIG. 7A, an increased amount of processing may occur at the sensor so as to reduce the amount of data needing to be transferred over a private network 1008 in real-time to a computing platform. The enhanced sensor system may filter at the sensor itself the measured/collected/captured data and only particular, filtered data may be transmitted to the data collection platform 1002 for storage and/or analysis.

Referring to FIG. 7B, in one or more embodiments, a data collection platform 1002 may include one or more processors 1060, one or more memories 1062, and communication interfaces 1068. The memory 1062 may include a database 1064 for storing data records of various values collected from one or more sources. In addition, a data collection module 1066 may be stored in the memory 1062 and assist the processor 1060 in the data collection platform 1002 in communicating with, via the communications interface 1068, one or more sensor, measurement, and data capture systems, and processing the data received from these sources. In some embodiments, the data collection module 1066 may include computer-executable instructions that, when executed by the processor 1060, cause the data collection platform 1002 to perform one or more of the steps disclosed herein. In other embodiments, the data collection module 1066 may be a hybrid of software-based and/or hardware-based instructions to perform one or more of the steps disclosed herein. In some examples, the data collection module 1066 may assist an enhanced sensor system with further filtering the measurements and readings collected from the sensor devices. Although the elements of FIG. 7B are illustrated as logical block diagrams, the disclosure is not so limited. In particular, one or more of the logical boxes in FIG. 7B may be combined into a single logical box or the functionality performed by a single logical box may be divided across multiple existing or new logical boxes. Moreover, some logical boxes that are visually presented as being inside of another logical box may be moved such that they are partially or completely residing outside of that logical box. For example, while the database 1064 in FIG. 7B is illustrated as being stored inside one or more memories 1062 in the data collection platform 1002, FIG. 7B contemplates that the database 1064 may be stored in a standalone data store communicatively coupled to the data collection module 1066 and processor 1060 of the data collection platform 1002 via the communications interface 1068 of the data collection platform 1002.

In addition, the data collection module 1066 may assist the processor 1060 in the data collection platform 1002 in communicating with, via the communications interface 1068, and processing data received from other sources, such as data feeds from third-party servers and manual entry at the field site from a dashboard graphical user interface (e.g., via dashboard 1003). For example, a third-party server may provide contemporaneous weather data to the data collection module. Some elements of chemical and petrochemical/ refinery plants may be exposed to the outside and thus may be exposed to various environmental stresses. Such stresses may be weather related such as temperature extremes (hot and cold), high wind conditions, and precipitation conditions such as snow, ice, and rain. Other environmental conditions may be pollution particulates such as dust and pollen, or salt if located near an ocean, for example. Such stresses can affect the performance and lifetime of equipment in the plants. Different locations may have different environmental stresses. For example, a refinery in Texas will have different stresses than a chemical plant in Montana. In another example, data manually entered from a dashboard graphical user interface (e.g., via dashboard 1003) (or other means) may be collected and saved into memory by the data collection module. Production rates may be entered and saved in memory. Tracking production rates may indicate issues with flows. For example, as fouling occurs, the production rate may fall if a specific outlet temperature can no longer be achieved at the targeted capacity and capacity has to be reduced to maintain the targeted outlet temperature.

Referring to FIG. 7C, in one or more embodiments, a data analysis platform 1004 may include one or more processors

1070, one or more memories 1072, and communication interfaces 1082. The memory 1072 may include a database 1074 for storing data records of various values collected from one or more sources. Alternatively or additionally, the database 1074 may be the same database as that depicted in FIG. 7B and the data analysis platform 1004 may communicatively couple with the database 1074 via the communication interface of the data analysis platform 1004. At least one advantage of sharing a database between the two platforms is the reduced memory requirements due to not duplicating the same or similar data. In addition, a data analysis module 1076 may be stored in the memory 1072 and assist the processor 1070 in the data analysis platform 1004 in processing and analyzing the data values stored in the database 1074. In some embodiments, the data analysis module 1076 may include computer-executable instructions that, when executed by the processor 1070, cause the data analysis platform 1004 to perform one or more of the steps disclosed herein. In other embodiments, the data analysis module 1076 may be a hybrid of software-based and/or hardware-based instructions to perform one or more of the steps disclosed herein. In some embodiments, the data analysis module 1076 may perform statistical analysis, predictive analytics, and/or machine learning on the data values in the database 1074 to generate predictions and models. For example, the data analysis platform 1004 may analyze sensor data to detect new problems and/or to monitor existing problems (e.g., to determine if an existing problem is growing, maintaining the same severity, or shrinking) in the equipment of a plant. The data analysis platform 1004 may compare temperature or other data from different dates to determine if changes are occurring. Such comparisons may be made on a monthly, weekly, daily, hourly, real-time, or some other basis.

Referring to FIG. 7C, the recommendation module 1078 in the data analysis platform 1004 may coordinate with the data analysis module 1076 to generate recommendations for adjusting one or more parameters for the operation of the plant environment depicted in FIG. 7A. In some embodiments, the recommendation module 1078 may communicate the recommendation to the command module 1080, which may generate command codes that may be transmitted, via the communications interface, to cause adjustments or halting/starting of one or more operations in the plant environment. The command codes may be transmitted to a control platform 1006 for processing and/or execution. In one or more embodiments, the command codes may be directly communicated, either wirelessly or in a wired fashion, to physical components at the plant such that the physical components include an interface to receive the commands and execute on them.

Although the elements of FIG. 7C are illustrated as logical block diagrams, the disclosure is not so limited. In particular, one or more of the logical boxes in FIG. 7C may be combined into a single logical box or the functionality performed by a single logical box may be divided across multiple existing or new logical boxes. Moreover, some logical boxes that are visually presented as being inside of another logical box may be moved such that they are partially or completely residing outside of that logical box. For example, while the database is visually depicted in FIG. 7C as being stored inside one or more memories in the data analysis platform 1004, FIG. 7C contemplates that the database may be stored in a standalone data store communicatively coupled to the data analysis module and processor of the data analysis platform 1004 via the communications interface of the data analysis platform 1004. Furthermore, the databases from multiple plant locations may be shared and holistically analyzed to identify one or more trends and/or patterns in the operation and behavior of the plant and/or plant equipment. In such a crowdsourcing-type example, a distributed database arrangement may be provided where a logical database may simply serve as an interface through which multiple, separate databases may be accessed. As such, a computer with predictive analytic capabilities may access the logical database to analyze, recommend, and/or predict the behavior of one or more aspects of plants and/or equipment. In another example, the data values from a database from each plant may be combined and/or collated into a single database where predictive analytic engines may perform calculations and prediction models.

Referring to FIG. 7D, in one or more embodiments, a control platform 1006 may include one or more processors 1084, one or more memories 1086, and communication interfaces 1092. The memory 1086 may include a database 1088 for storing data records of various values transmitted from a user interface, computing device, or other platform. The values may include parameter values for particular equipment at the plant. For example, some illustrative equipment at the plant that may be configured and/or controlled by the control platform 1006 include, but is not limited to, a feed switcher 1042, sprayer 1052, one or more valves 1044, one or more pumps 1040, one or more gates 1048, and/or one or more drains 1050. In addition, a control module 1090 may be stored in the memory and assist the processor in the control platform 1006 in receiving, storing, and transmitting the data values stored in the database. In some embodiments, the control module 1090 may include computer-executable instructions that, when executed by the processor 1084, cause the control platform 1006 to perform one or more of the steps disclosed herein. In other embodiments, the control module may be a hybrid of software-based and/or hardware-based instructions to perform one or more of the steps disclosed herein.

In a plant environment such as illustrated in FIG. 7A, if sensor data is outside of a safe range, this may be cause for immediate danger. As such, there may be a real-time component to the system such that the system processes and responds in a timely manner. Although in some embodiments, data could be collected and leisurely analyzed over a lengthy period of months, numerous embodiments contemplate a real-time or near real-time responsiveness in analyzing and generating alerts, such as those generated or received by the alert module in FIG. 7E.

Referring to FIG. 7E, in one or more embodiments, a remote device 1054 may include one or more processors 1093, one or more memories 1094, and communication interfaces 1099. The memory 1094 may include a database 1095 for storing data records of various values entered by a user or received through the communications interface. In addition, an alert module 1096, command module 1097, and/or dashboard module 1098 may be stored in the memory 1094 and assist the processor 1093 in the remote device 1054 in processing and analyzing the data values stored in the database. In some embodiments, the aforementioned modules may include computer-executable instructions that, when executed by the processor, cause the remote device 1054 to perform one or more of the steps disclosed herein. In other embodiments, the aforementioned modules may be a hybrid of software-based and/or hardware-based instructions to perform one or more of the steps disclosed herein. In some embodiments, the aforementioned modules may generate alerts based on values received through the communications interface. The values may indicate a dangerous condition or even merely a warning condition due to odd sensor readings. The command module 1097 in the remote device 1054 may generate a command that when transmitted through the communications interface to the platforms at the plant, causes adjusting of one or more parameter operations of the plant environment depicted in FIG. 7A. In some embodiments, the dashboard module 1098 may display a graphical user interface to a user of the remote device 1054 to enable the user to enter desired parameters and/or commands. These parameters/commands may be transmitted to the command module 1097 to generate the appropriate resulting command codes that may be then transmitted, via the communications interface, to cause adjustments or halting/starting of one or more operations in the plant environment. The command codes may be transmitted to a control platform 1006 for processing and/or execution. In one or more embodiments, the command codes may be directly communicated, either wirelessly or in a wired fashion, to physical components at the plant such that the physical components include an interface to receive the commands and execute them.

Although FIG. 7E is not so limited, in some embodiments the remote device 1054 may include a desktop computer, a smartphone, a wireless device, a tablet computer, a laptop computer, and/or the like. The remote device 1054 may be physically located locally or remotely, and may be connected by one of communications links to the public network 1010 that is linked via a communications link to the private network 1008. The network used to connect the remote device 1054 may be any suitable computer network including the Internet, an intranet, a wide-area network (WAN), a local-area network (LAN), a wireless network, a digital subscriber line (DSL) network, a frame relay network, an asynchronous transfer mode (ATM) network, a virtual private network 1008 (VPN), or any combination of any of the same. Communications links may be any communications links suitable for communicating between workstations and server, such as network links, dial-up links, wireless links, hard-wired links, as well as network types developed in the future, and the like. Various protocols such as transmission control protocol/Internet protocol (TCP/IP), Ethernet, file transfer protocol (FTP), hypertext transfer protocol (HTTP) and the like may be used, and the system can be operated in a client-server configuration to permit a user to retrieve web pages from a web-based server. Any of various conventional web browsers can be used to display and manipulate data on web pages.

Although the elements of FIG. 7E are illustrated as logical block diagrams, the disclosure is not so limited. In particular, one or more of the logical boxes in FIG. 7E may be combined into a single logical box or the functionality performed by a single logical box may be divided across multiple existing or new logical boxes. Moreover, some logical boxes that are visually presented as being inside of another logical box may be moved such that they are partially or completely residing outside of that logical box. For example, while the database is visually depicted in FIG. 7E as being stored inside one or more memories in the remote device 1054, FIG. 7E contemplates that the database may be stored in a standalone data store communicatively coupled, via the communications interface, to the modules stored at the remote device 1054 and processor of the remote device 1054.

Referring to FIGS. 7A to 7E, in some examples, the performance of operation in a plant may be improved by using a cloud computing infrastructure and associated methods, as described in US Patent Application Publication No. US2016/0260041, which was published Sep. 8, 2016, and which is herein incorporated by reference in its entirety. The methods may include, in some examples, obtaining plant operation information from the plant and/or generating a plant process model using the plant operation information. The method may include receiving plant operation information over the Internet, or other computer network (including those described herein) and automatically generating a plant process model using the plant operation information. These plant process models may be configured and used to monitor, predict, and/or optimize performance of individual process units, operating blocks and/or complete processing systems. Routine and frequent analysis of predicted versus actual performance may further allow early identification of operational discrepancies, which may be acted upon to optimize impact.

The aforementioned cloud computing infrastructure may use a data collection platform 1002 associated with a plant to capture data, e.g., sensor measurements, which may be automatically sent to the cloud infrastructure, which may be remotely located, where it may be reviewed to, for example, eliminate errors and biases, and used to calculate and report performance results. The data collection platform 1002 may include an optimization unit that acquires data from a customer site, other site, and/or plant (e.g., sensors and other data collectors at a plant) on a recurring basis. For cleansing, the data may be analyzed for completeness and corrected for gross errors by the optimization unit. The data may also be corrected for measurement issues (e.g., an accuracy problem for establishing a simulation steady state) and overall mass balance closure to generate a duplicate set of reconciled plant data. The corrected data may be used as an input to a simulation process, in which the process model is tuned to ensure that the simulation process matches the reconciled plant data. An output of the reconciled plant data may be used to generate predicted data using a collection of virtual process model objects as a unit of process design.

The performance of the plant and/or individual process units of the plant is/are compared to the performance predicted by one or more process models to identify any operating differences or gaps. Furthermore, the process models and collected data (e.g., plant operation information) may be used to run optimization routines that converge on an optimal plant operation for a given values of, e.g., feed, products, and/or prices. A routine may be understood to refer to a sequence of computer programs or instructions for performing a particular task.

The data analysis platform 1004 may include an analysis unit that determines operating status, based on at least one of a kinetic model, a parametric model, an analytical tool, and/or a related knowledge and/or best practice standard. The analysis unit may receive historical and/or current performance data from one or a plurality of plants to proactively predict one or more future actions to be performed. To predict various limits of a particular process and stay within the acceptable range of limits, the analysis unit may determine target operational parameters of a final product based on actual current and/or historical operational parameters. This evaluation by the analysis unit may be used to proactively predict future actions to be performed. In another example, the analysis unit may establish a boundary or threshold of an operating parameter of the plant based on at least one of an existing limit and an operation condition. In yet another example, the analysis unit may establish a relationship between at least two operational parameters related to a specific process for the operation of the plant.

Finally in yet another example, one or more of the aforementioned examples may be performed with or without a combination of the other examples.

The plant process model predicts plant performance that is expected based upon the plant operation information. The plant process model results can be used to monitor the health of the plant and to determine whether any upset or poor measurement occurred. The plant process model is desirably generated by an iterative process that models at various plant constraints to determine the desired plant process model.

Using a web-based system for implementing the method of this disclosure may provide one or more benefits, such as improved plant performance due to an increased ability by plant operators to identify and capture opportunities, a sustained ability to bridge plant performance gaps, and/or an increased ability to leverage personnel expertise and improve training and development. Some of the methods disclosed herein allow for automated daily evaluation of process performance, thereby increasing the frequency of performance review with less time and effort required from plant operations staff.

Further, the analytics unit may be partially or fully automated. In one or more embodiments, the system is performed by a computer system, such as a third-party computer system, remote from the plant and/or the plant planning center. The system may receive signals and parameters via the communication network, and displays in real time related performance information on an interactive display device accessible to an operator or user. The web-based platform allows all users to work with the same information, thereby creating a collaborative environment for sharing best practices or for troubleshooting. The method further provides more accurate prediction and optimization results due to fully configured models. Routine automated evaluation of plant planning and operation models allows timely plant model tuning to reduce or eliminate gaps between plant models and the actual plant performance. Implementing the aforementioned methods using the web-based platform also allows for monitoring and updating multiple sites, thereby better enabling facility planners to propose realistic optimal targets.

Figure 8B:
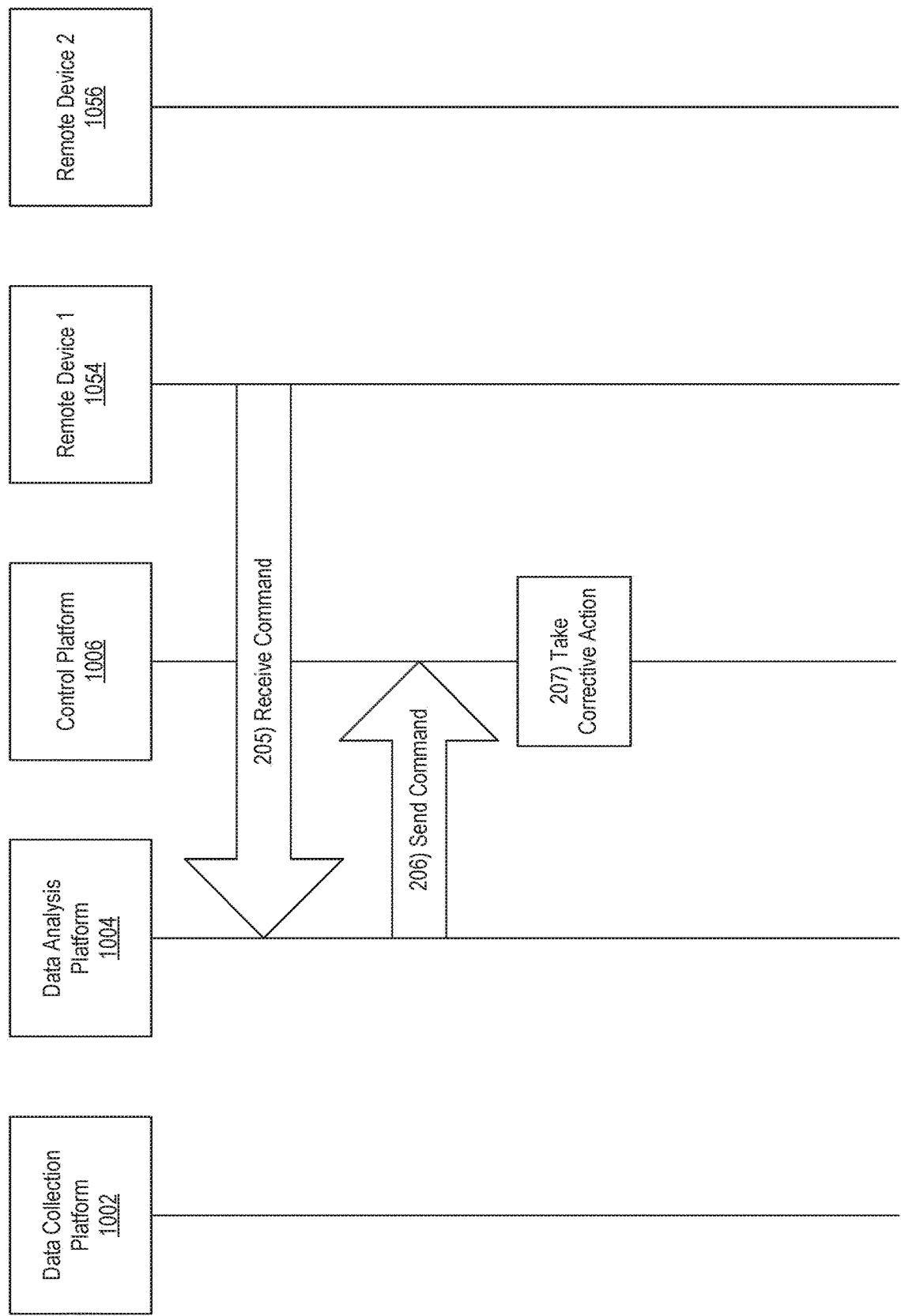

FIGS. 8A and 8B depict illustrative system flow diagrams in accordance with one or more embodiments described herein. As shown in FIG. 8A, in step 201, data collection platform 1002 may collect sensor data. In step 202, data collection platform 1002 may transmit sensor data to data analysis platform 1004. In step 203, data analysis platform 1004 may analyze data. In step 204, data analysis platform 1004 may send an alert to remote device 1054 and/or remote device 1056.

As shown in FIG. 8B, in step 205, data analysis platform 1004 may receive a command from remote device 1054 and/or remote device 1056. In some embodiments, the control platform 1006 may receive the command from remote device 1054 and/or remote device 1056. In step 206, data analysis platform 1004 may send a command to control platform 1006. In some embodiments, the command may be similar to the command received from remote device 1054 and/or remote device 1056. In some embodiments, data analysis platform 1004 may perform additional analysis based on the received command from remote device 1054 and/or remote device 1056 before sending a command to control platform 1006. In step 207, control platform 1006 may take corrective action. The corrective action may be based on the command received from data analysis platform 1004, remote device 1054, and/or remote device 1056. The corrective action may be related to one or more pieces of equipment (e.g., rotating equipment) associated with sensors that collected the sensor data in step 201.

Figure 11:
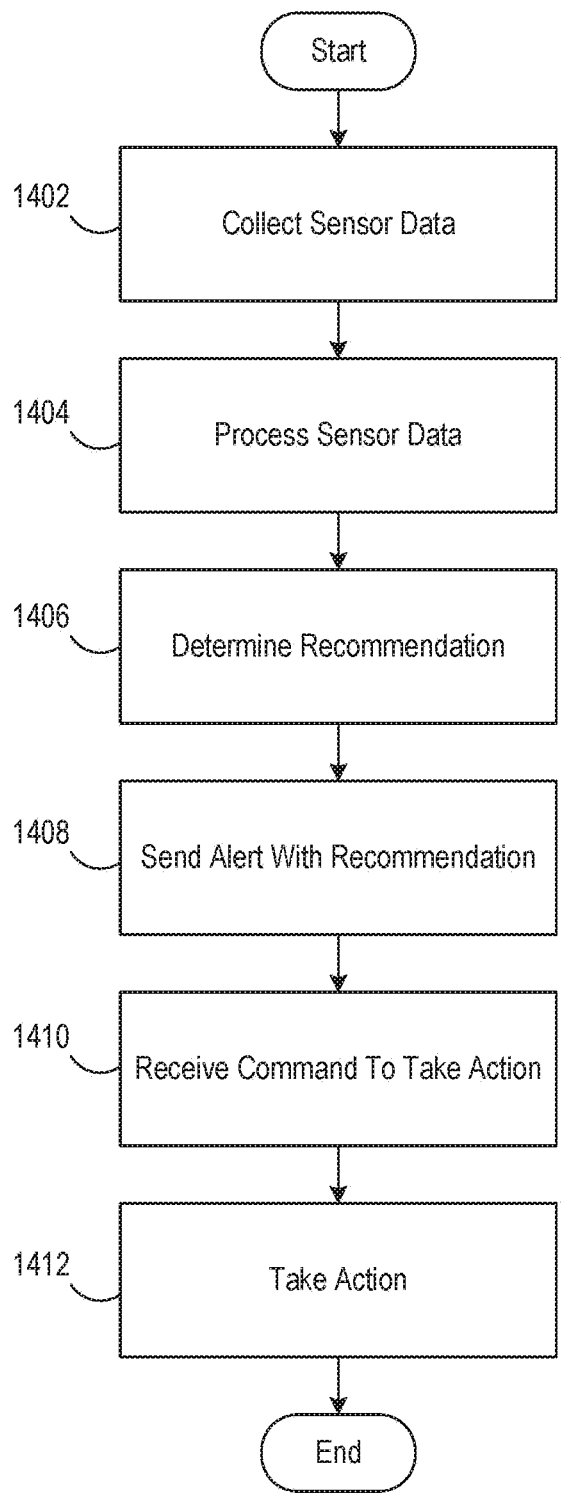
FIG. 11 depicts an illustrative flowchart of a process that one or more devices may perform in controlling one or more aspects of a plant operation in accordance with one or more example embodiments.
Figure 11A:
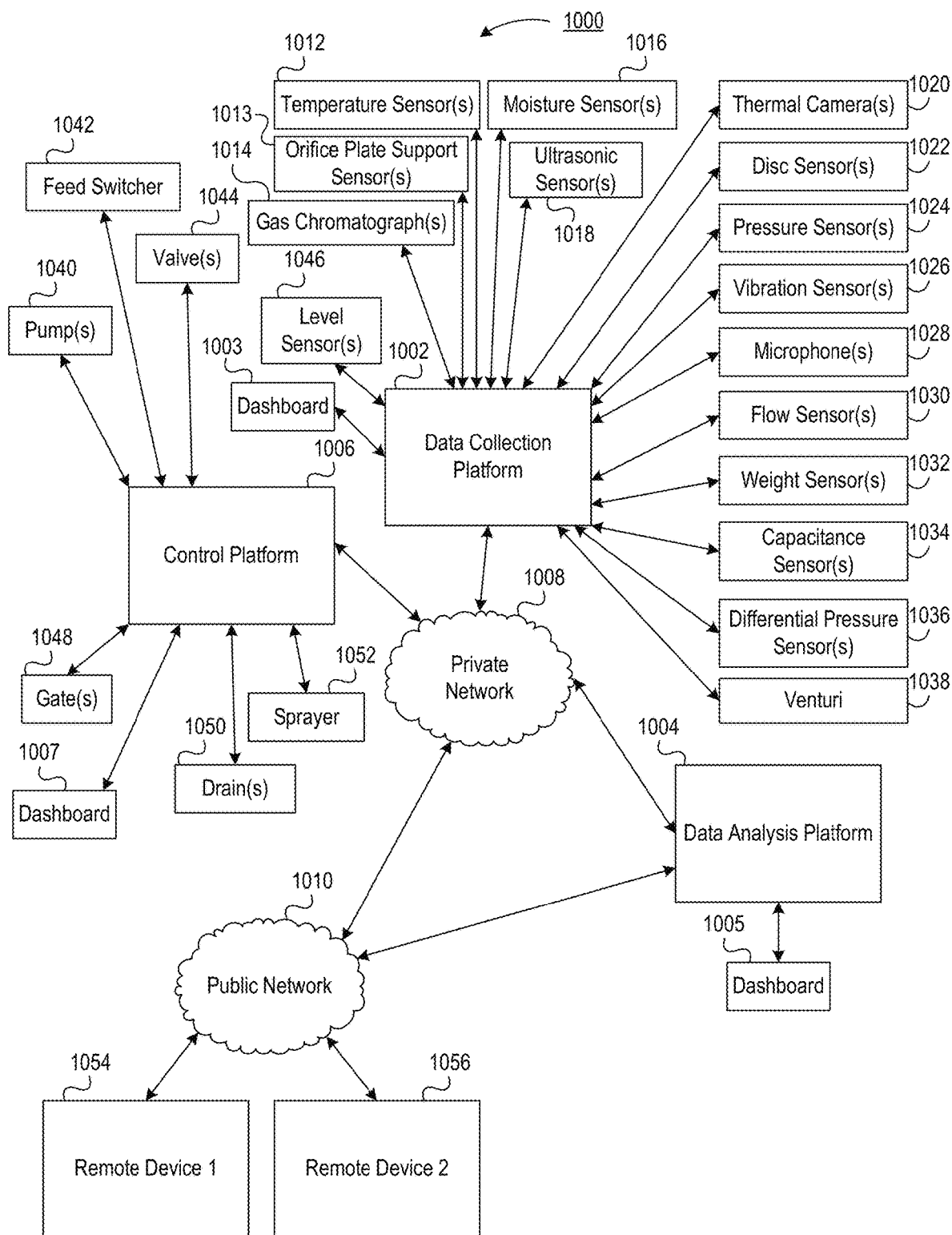
Figure 11B:
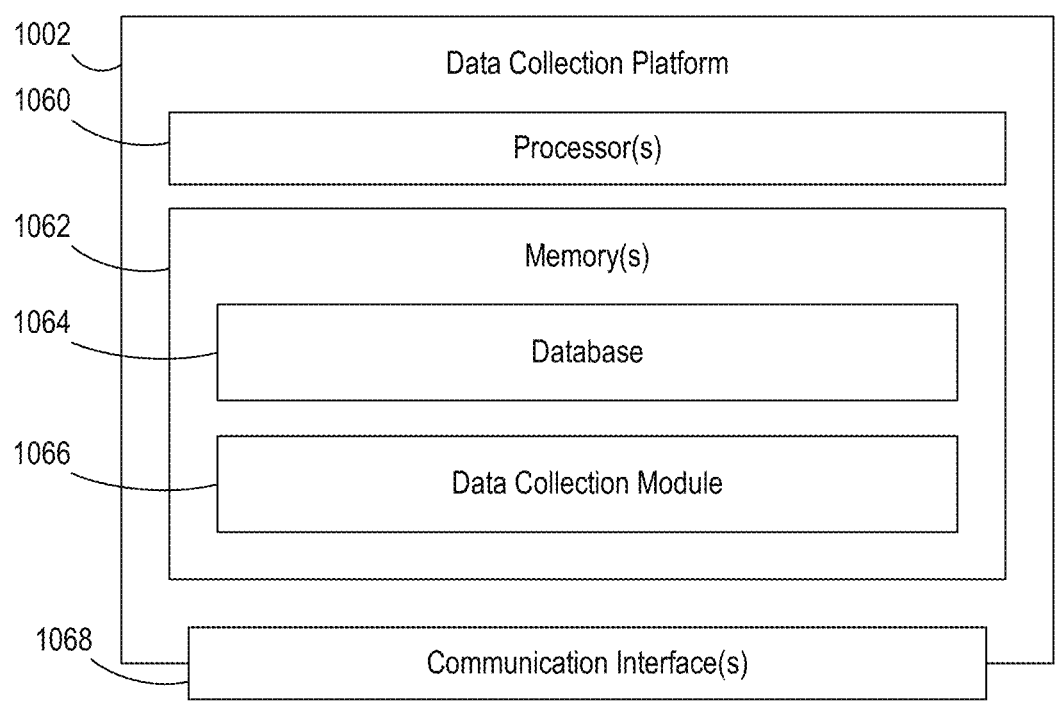
Figure 11C:
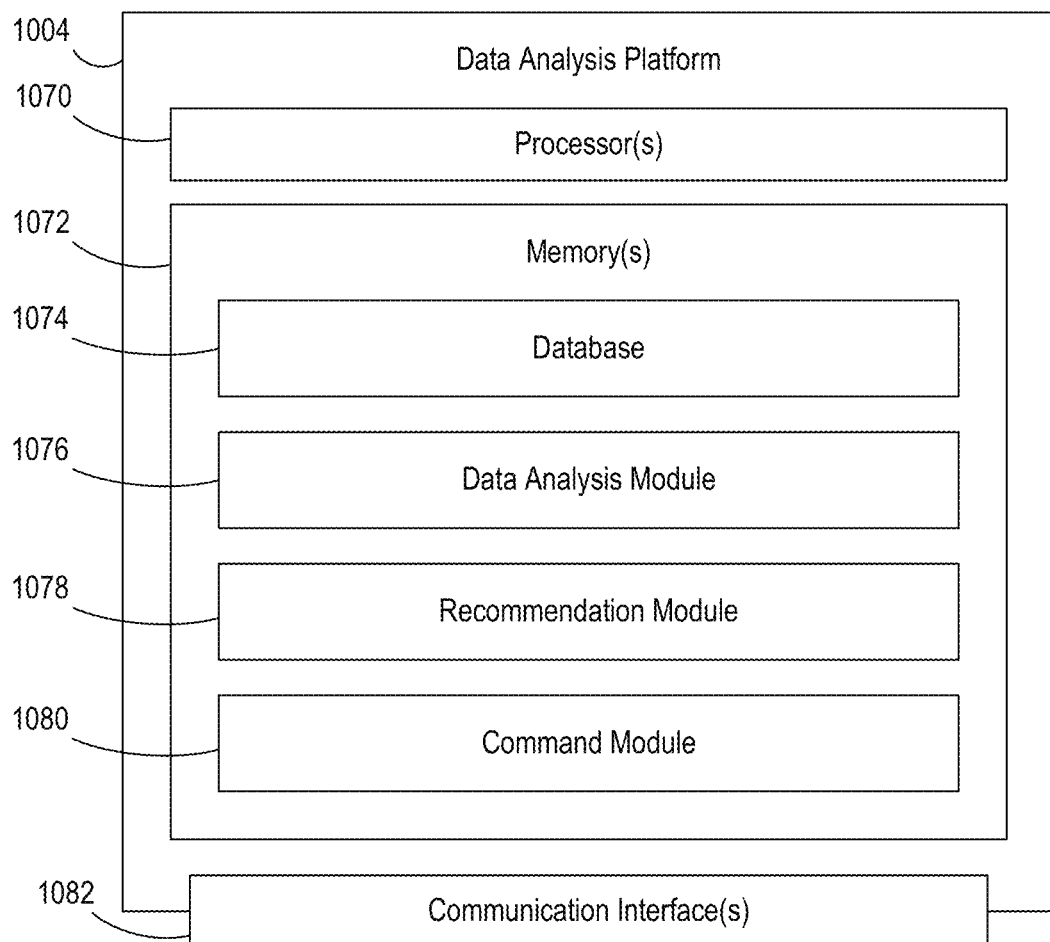
Figure 11D:
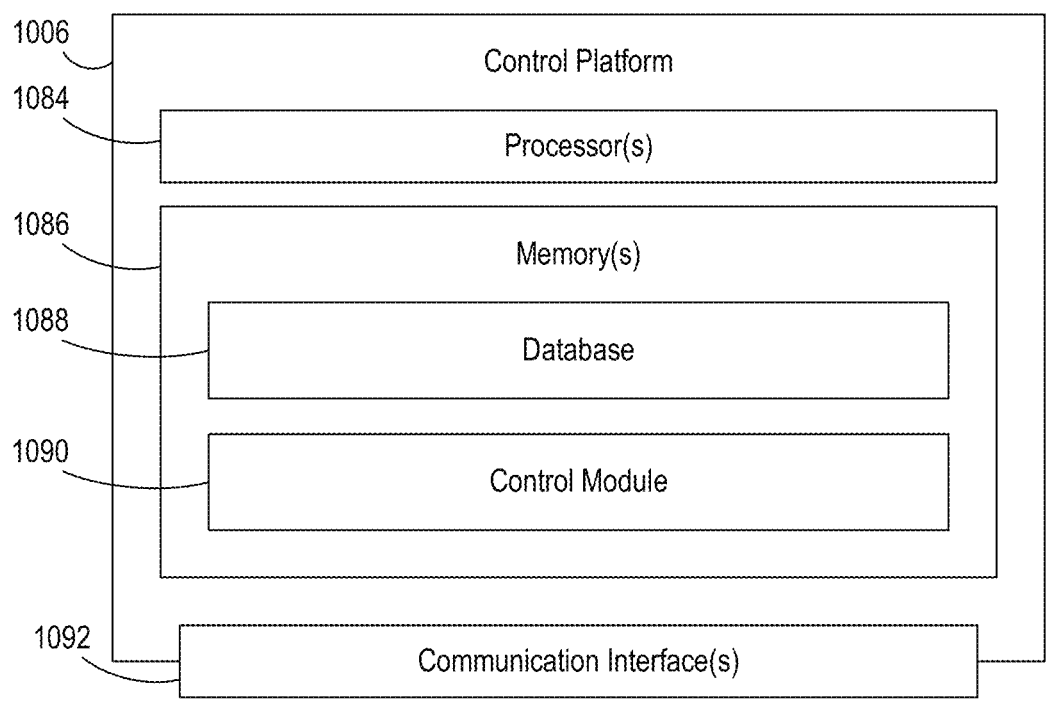
Figure 11E:
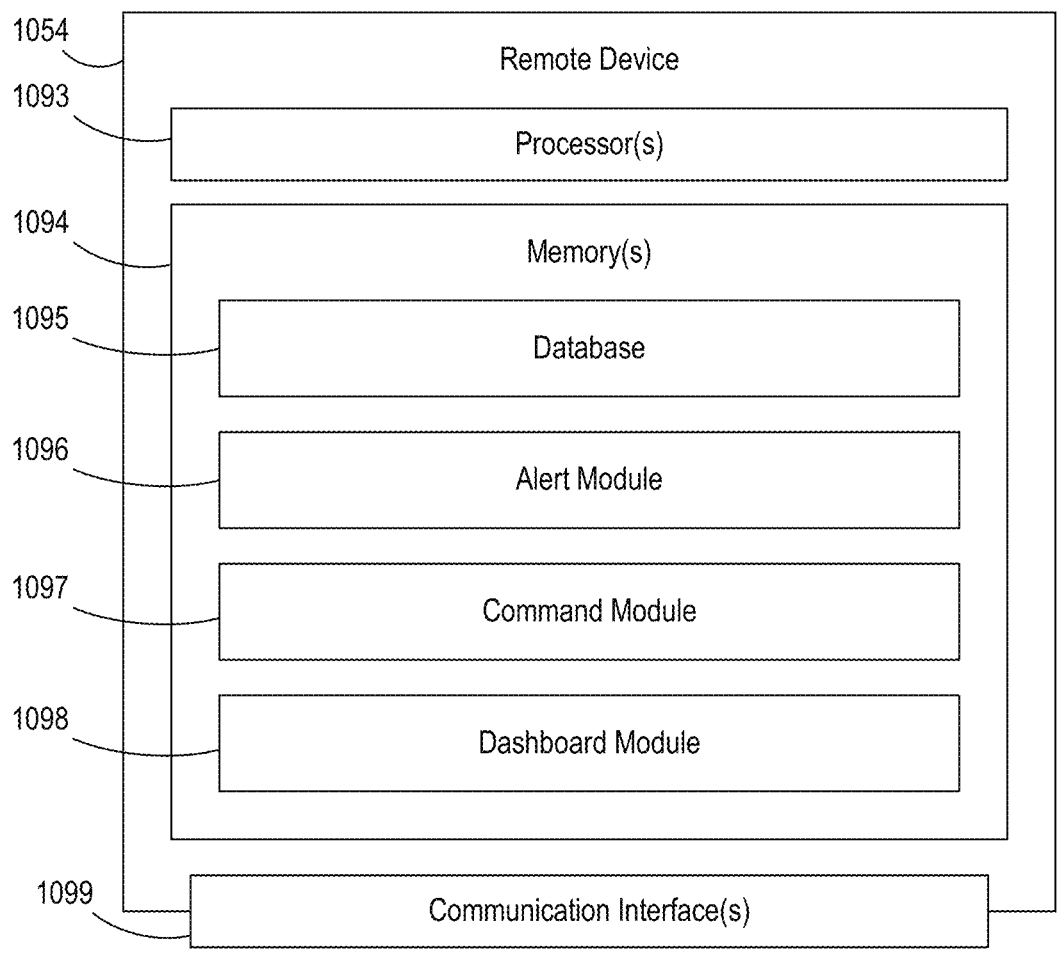
Figure 13:
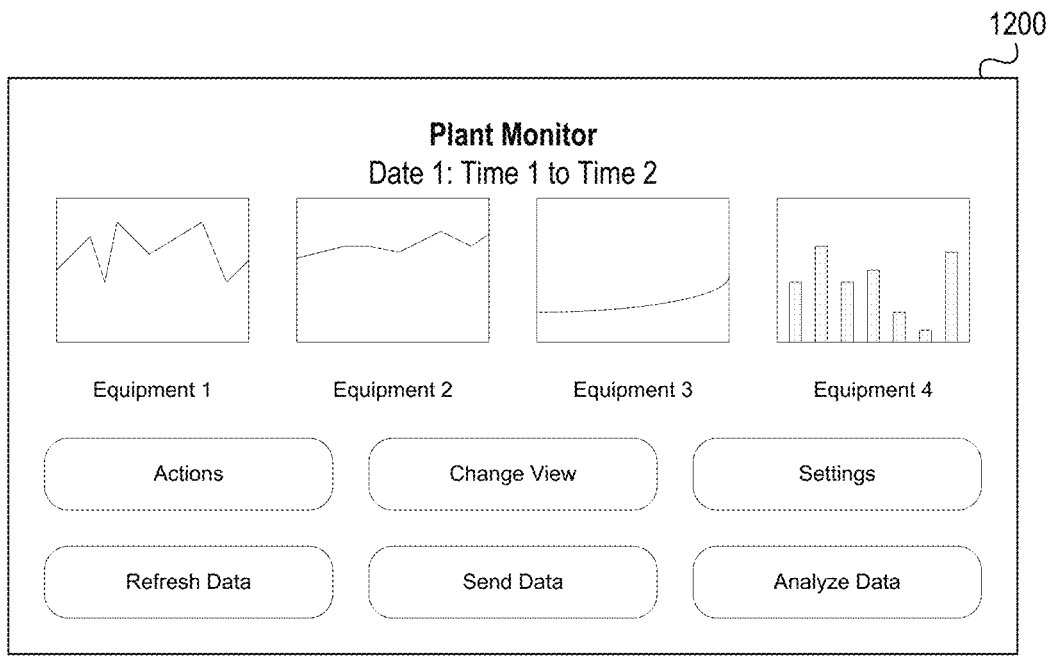
Figure 14:
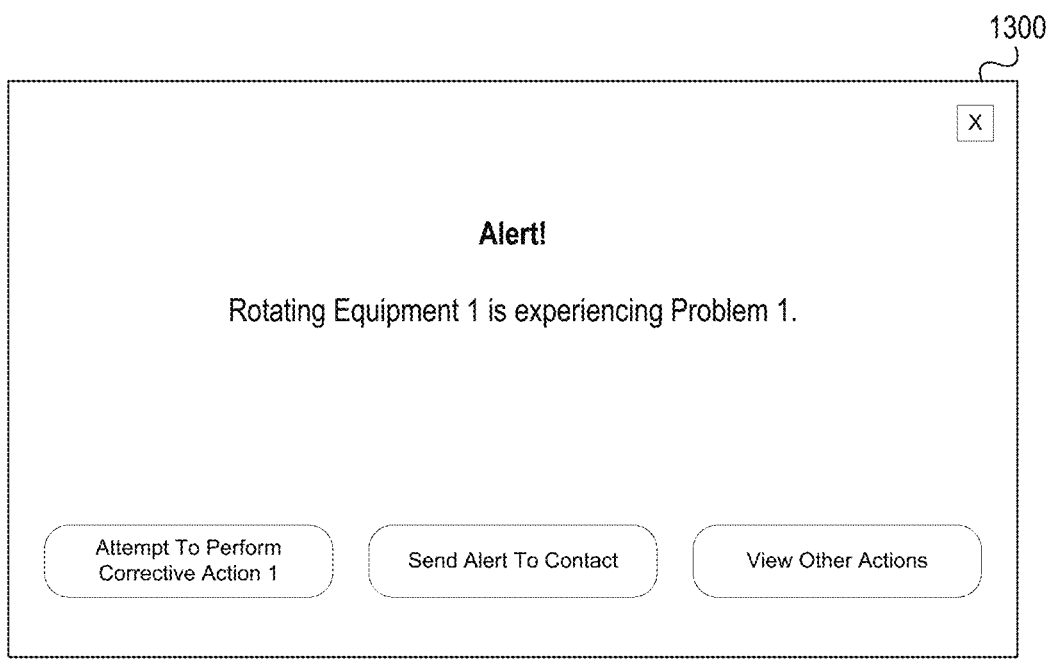
Figure 15:
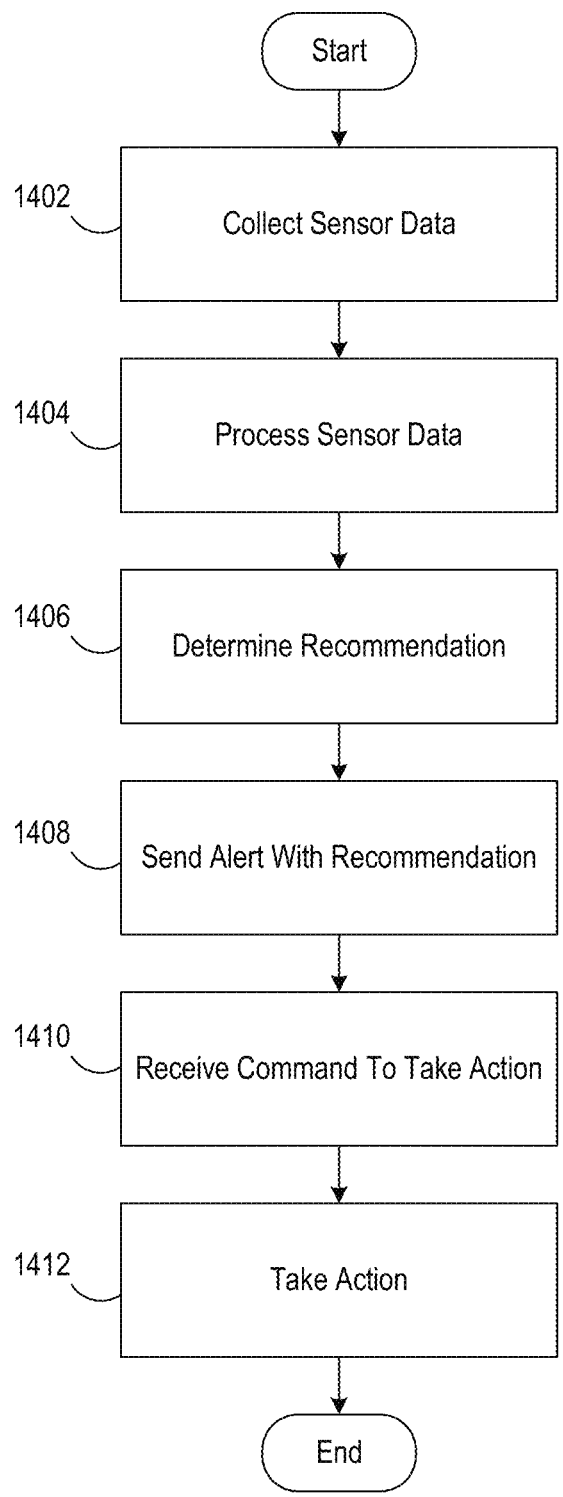

FIG. 11 depicts an illustrative flow diagram in accordance with one or more embodiments described herein. The flow may be performed by one or more devices, which may be interconnected via one or more networks.

First, the one or more devices may collect 1402 sensor data. The sensor data may be from one or more sensors attached to one or more pieces of equipment (e.g., rotating equipment) in a plant. The sensor data may be locally collected and processed and/or may be locally collected and transmitted for processing.

After the sensor data is collected, the one or more devices may process 1404 the sensor data. The one or more devices may compare the data to past data from the one or more pieces of equipment, other pieces of equipment at a same plant, one or more pieces of equipment at a different plant, manufacturer recommendations or specifications, or the like.

After the sensor data is processed, the one or more devices may determine 1406 one or more recommendations based on the sensor data. The one or more recommendations may include recommendations of one or more actions to take based on the sensor data.

The one or more devices may send 1408 one or more alerts, which may include the determined recommendation. The one or more alerts may include information about the sensor data, about other data, or the like.

The one or more devices may receive 1410 a command to take an action (e.g., the recommended action, an action other than the recommended action, or no action). After receiving the command, the one or more devices may take 1412 the action. The action may, in some embodiments, include one or more corrective actions, which may cause one or more changes in the operation of the one or more pieces of equipment. The corrective action(s) may be taken automatically or after user confirmation, and/or the corrective action(s) may be taken without an accompanying alert being generated (and vice-versa).

Figure 9:
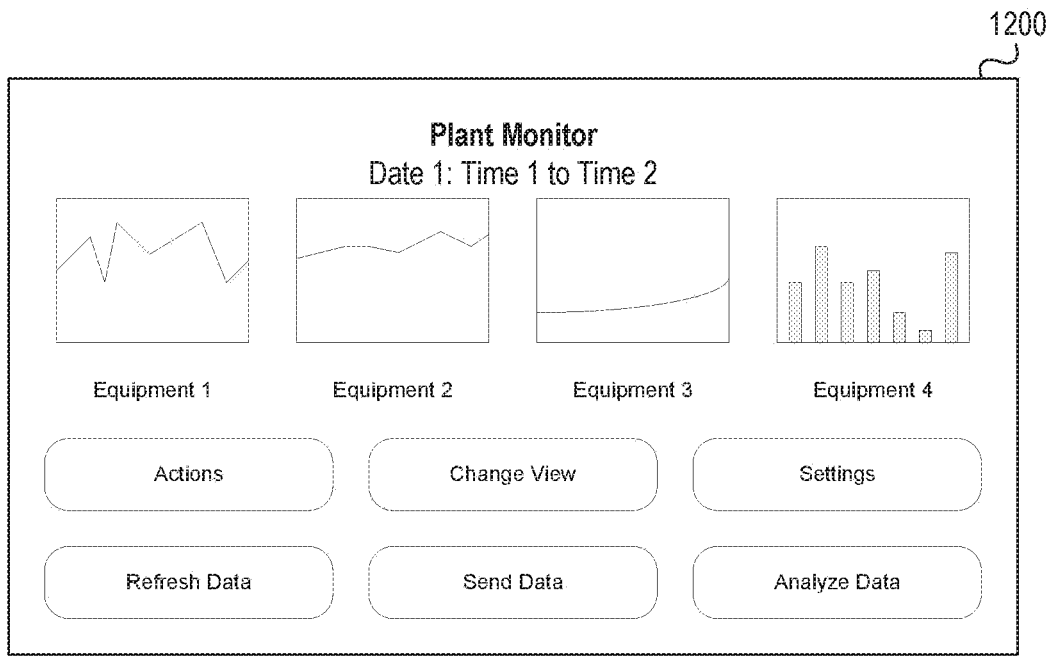
FIGS. 9 and 10 depict illustrative graphical user interfaces related to one or more aspects of a plant operation in accordance with one or more example embodiments.

FIG. 9 depicts an illustrative graphical user interface 1200 of an application that may be used for providing information received from one or more sensors or determined based on analyzing information received from one or more sensors, according to one or more embodiments described herein. The graphical user interface may be displayed as part of a smartphone application (e.g., running on a remote device, such as remote device 1054 or remote device 1056), a desktop application, a web application (e.g., that runs in a web browser), a web site, an application running on a plant computer, or the like.

The graphical user interface 1200 may include one or more visual representations of data (e.g., chart, graph, etc.) that shows information about a plant, a particular piece of equipment in a plant, or a process performed by a plant or a particular piece or combination of equipment in the plant. For example, a graph may show information about an operating condition, an efficiency, a production level, or the like. The graphical user interface 1200 may include a description of the equipment, the combination of equipment, or the plant to which the visual display of information pertains.

The graphical user interface 1200 may display the information for a particular time or period of time (e.g., the last five minutes, the last ten minutes, the last hour, the last two hours, the last 12 hours, the last 24 hours, etc.). The graphical user interface may be adjustable to show different ranges of time, automatically or based on user input.

The graphical user interface 1200 may include one or more buttons that allow a user to take one or more actions. For example, the graphical user interface may include a button (e.g., an "Actions" button) that, when pressed, shows one or more actions available to the user. The graphical user interface may include a button (e.g., a "Change View" button) that, when pressed, changes one or more views of one or more elements of the graphical user interface. The graphical user interface may include a button (e.g., a "Settings" button) that, when pressed, shows one or more settings of the application of which the graphical user interface is a part. The graphical user interface may include a button (e.g., a "Refresh Data" button) that, when pressed, refreshes data displayed by the graphical user interface. In some aspects, data displayed by the graphical user interface may be refreshed in real time, according to a preset schedule (e.g., every five seconds, every ten seconds, every minute, etc.), and/or in response to a refresh request received from a user. The graphical user interface may include a button (e.g., a "Send Data" button) that, when pressed, allows a user to send data to one or more other devices. For example, the user may be able to send data via email, SMS, text message, iMessage, FTP, cloud sharing, AirDrop, or via some other method. The user may be able to select one or more pieces of data, graphics, charts, graphs, elements of the display, or the like to share or send. The graphical user interface may include a button (e.g., an "Analyze Data" button) that, when pressed, causes one or more data analysis functions to be performed. In some aspects, the user may provide additional input about the desired data analysis, such as desired input, desired output, desired granularity, desired time to complete the data analysis, desired time of input data, or the like.

Figure 10:
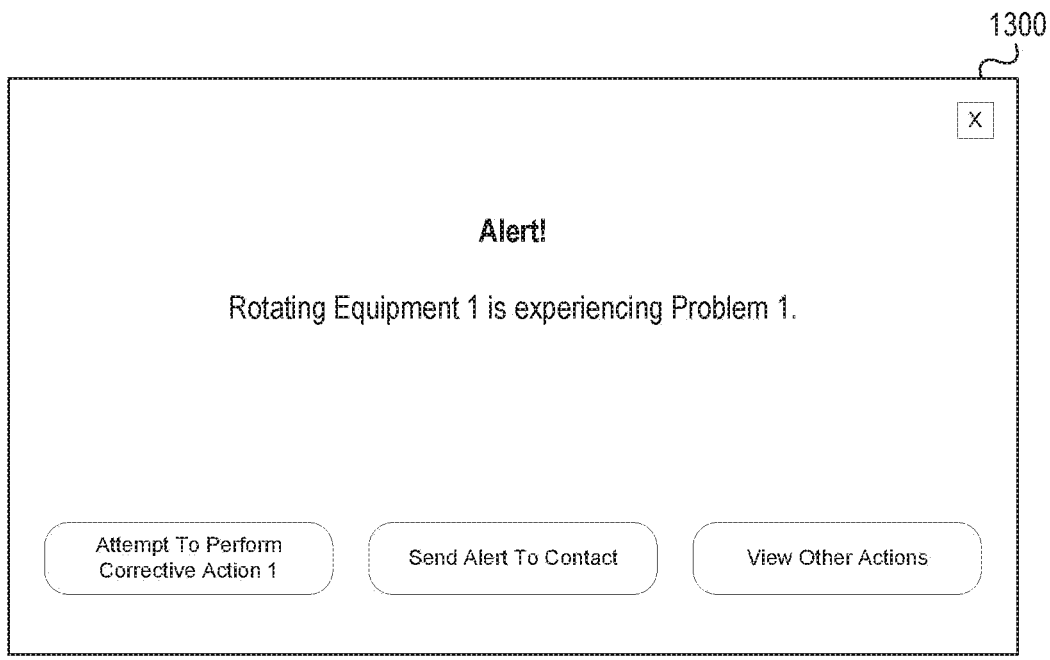

FIG. 10 depicts an illustrative graphical user interface 1300 of an application that may be used for providing alerts and/or receiving or generating commands for taking corrective action, in accordance with one or more embodiments described herein. The graphical user interface 1300 may include an alert with information about a current state of a piece of equipment (e.g., rotating equipment), a problem being experienced by a piece of equipment (e.g., rotating equipment), a problem with a plant, or the like.

The graphical user interface 1300 may include one or more buttons that, when pressed, cause one or more actions to be taken. For example, the graphical user interface 1300 may include a button that, when pressed, causes a flow rate to change. In another example, the graphical user interface 1300 may include a button that, when pressed, sends an alert to a contact (e.g., via a remote device), the alert including information similar to the information included in the alert provided via the graphical user interface. In a further example, the graphical user interface 1300 may include a button that, when pressed, shows one or more other actions that may be taken (e.g., additional corrective actions).

Gas Quality for Dynamic Compressors

In one or more embodiments, sensors at various locations within the system can be used to measure various properties of the gas within the system, and this data is analyzed to determine the quality of the gas in the system. The computer system may take actions, such as generating alerts or initiating corrective action, based on the determined gas quality. The dry gas seals of a centrifugal compressor are one component at particular risk of failure from liquid condensation due to poor gas quality, and altering the gas flow may be necessary to avoid failure of the dry gas seals.

Several different combinations of sensors and techniques may be used to determine the composition of the gas in the system. In one or more embodiments, a gas chromatograph may be used to directly measure composition of the gas, although this may not permit continuous and real-time measurement. In another example, the density of the gas may be measured using a mass flow meter (e.g., a Coriolis mass flow meter), and the composition of the gas may be inferred from the density. In another example, a thermal mass meter may be used to measure heat capacity of the gas, and the composition of the gas may be inferred from the heat capacity. In another example, the temperature at the separator may be measured, and the amount of heavy gases (e.g., benzene) in the process gas may be inferred from the temperature in the separator. Other sensors, such as flow, pressure, and temperature sensors may aid in the determination or inferring of gas composition. The computer system receives data gathered according to one or more of these sensor configurations and analyzes the data to determine the composition of the gas using these methods.

Once the composition of the gas is determined, the computer system can determine whether the composition is indicative of the present or future occurrence of an issue such as condensation or component (e.g., seal) failure, and take actions if appropriate based on the determination. The quantity of heavy components in the gas flow can be determined using analysis of the data described above, and this quantity can be compared to other operational data during analysis by the computer system as described below. Alternately, the computer system may base the analysis on the raw data, e.g., density, heat capacity, separator temperature, etc., rather than the inferred composition. The raw data may be more conducive to quantitative analysis in some circumstances. The analysis performed by the computer system may include modeling of the conditions in the treating system, including temperature and pressure, to predict whether condensation will occur based on the determined or inferred composition of the gas or the data from which the composition is inferred. The modeling may also be used to predict the dew point of the gas and/or the amount of condensation of the gas, which can be used in quantitative analysis to determine a deviation from normal operating conditions or other indication of present or future condensation.

Sensor information may be gathered by one or more sensors and transmitted to data collection platform. Data collection platform may transmit the collected sensor data to data analysis platform, which may be at a plant or remote from a plant (e.g., in the cloud). Data analysis platform may analyze the received sensor data. Data analysis platform may compare the sensor data to one or more rules to determine if any of the issues disclosed herein are occurring. For example, poor gas quality may be indicated if one or more conditions are met: (1) inappropriate heat capacity of the gas as measured by a thermal mass meter, and/or (2) an inappropriate amount of heavy gas as inferred from the temperature measured in the separator. Furthermore, data analysis platform may compare current sensor data to past sensor data from the rotating equipment, from other rotating equipment at the same plant, from other rotating equipment at other plants, from a manufacturer, or the like. Data analysis platform may determine if one or more data characteristics of the sensor data match data that may indicate any of the issues disclosed herein.

Data analysis platform may further run process simulations to suggest changes to operating parameters of the rotating equipment and associated components to avoid or limit further damage by one or more of the issues disclosed herein. In some aspects, data analysis platform may communicate with one or more vendors regarding the results of the simulation, and receive recommendations from the vendor on how to change or optimize parameters (e.g., geometry) of the equipment. Data analysis platform may use this information to create or expand a searchable database.

In one or more embodiments, the collected data may be compared to current or archived data, and the computer system can analyze the data to make useful determinations, such as whether the data indicates that a potential gas quality issue exists or will exist and/or making predictions regarding future operation. The data comparison may be made across a variety of time frames, from a single point measurement, to a time frame of a few minutes or hours, to real-time continuous comparison, to historical comparison over a period of months or more, and may include absolute and proportional comparisons. As one example, a deviation from normal data may be detected if a component of the data is found to differ by a set percentage (e.g., +/−5% or 10%) from normal operation data. As another example, a deviation may be detected if the data exceeds a specific absolute threshold, either as a set threshold or as a set absolute difference from normal operation data. The data analysis may be done over one or more different time frames, and the deviation percentage or threshold may depend on the time frame for comparison. In one or more embodiments, the difference from normal operation data required to detect a deviation over a short time frame may be relatively large as compared to analysis of a longer time frame, which may require a relatively smaller difference to detect a deviation. For example, a gradual but consistent change in composition or other data over a long time frame may be used in predicting long-term failure.

The data comparison may also be made with respect to various different pieces of equipment. As one example, the data comparison may be limited to only the equipment or component in question. As another example, the data comparison may be made relative to other equipment or components in the system, and potentially to all other equipment and/or components of the same type within the system. As a further example, the data comparison may be made relative to historical data, including historical data for the same equipment or component, or historical data for other equipment or components. It is understood that data analysis does not necessarily need to be done for the purpose of detecting deviations, as described in greater detail below. For example, data comparison that indicates consistency with historical data for a piece of equipment or a component that failed in a specific way may be valuable in predicting whether and when condensation or component (e.g., seal) failure will occur.

The data used for the comparison may also depend on the stage of operation of the equipment or component. For example, start-up or shut-down of the machine may place increased stresses on the system and may require different data comparison. Different criteria (% or threshold) for deviation from normal operation may be applied during start-up or shut-down. Different comparison data may be used for analysis during start-up or shut-down as well, such as comparison to other start-up or shut-down data, rather than data from steady operation. As another example, different criteria and/or comparison data may be used during particular environmental conditions, such as based on a particular season or weather phenomenon.

In another example, the data can be compared to previous trend or pattern data from the same or other equipment or components. In this example, the overall trend or pattern of the data for the equipment or component may be analyzed to determine which previous data sets match most closely to the present data. Once one or more similar trends in data are matched, the matched data sets may provide useful predictive value. For example, matched data may be valuable in predicting whether and when condensation or component (e.g., seal) failure will occur and/or which solutions may be effectively implemented to address an actual or potential issue.

When the computer system determines that a present condensation or component failure exists or predicts the future occurrence of such an issue, the computer system can take actions accordingly, including generating alerts and/or initiating corrective actions. Examples of corrective actions to avoid condensation include changing the feed source for the gas flow and/or increasing the temperature of heaters. Another example of a corrective action is to process the gas to eliminate heavy components prone to condensation before the gas enters the heater or the compressor. This action requires the addition of a device upstream of the heater and/or the compressor to decrease the gas pressure to condense the heavy components and then re-pressurizes the remainder of the gas flow.

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one or more of the steps illustrated in the illustrative figures may be performed in other than the recited order, and one or more depicted steps may be optional in accordance with aspects of the disclosure.

What is claimed is:

1. A system comprising:
a reactor;
a heater;
a centrifugal compressor comprising a dry gas seal;
one or more sensors associated with the centrifugal compressor;
a data collection platform comprising:
  one or more processors of the data collection platform;
  a communication interface of the data collection platform; and
  computer-readable memory storing executable instructions that, when executed, cause the data collection platform to:
    receive, from the one or more sensors associated with the centrifugal compressor, sensor data associated with the centrifugal compressor and collected by the one or more sensors associated with the centrifugal compressor; and
    send the sensor data associated with the centrifugal compressor and collected by the one or more sensors associated with the centrifugal compressor; and
a data analysis platform comprising:
  one or more processors of the data analysis platform;
  a communication interface of the data analysis platform; and
  computer-readable memory storing executable instructions that, when executed, cause the data analysis platform to:
    receive the sensor data associated with the centrifugal compressor and collected by the one or more sensors associated with the centrifugal compressor;

analyze the sensor data associated with the centrifugal compressor to determine a composition of gas used in the centrifugal compressor;

determine, based on the composition of the gas used in the centrifugal compressor, a potential component failure of the centrifugal compressor; and based on determining the potential component failure of the centrifugal compressor, send a command configured to cause an adjustment to an operating parameter of the centrifugal compressor;

a temperature sensor among the one or more sensors associated with the centrifugal compressor, wherein the computer-readable memory of the data analysis platform stores executable instructions that, when executed, cause the data analysis platform to:

receive temperature information associated with the centrifugal compressor and collected by the temperature sensor; and analyze the temperature information to determine an amount of heavy gas in the gas used in the centrifugal compressor.

2. The system of claim 1, wherein the computer-readable memory of the data analysis platform stores executable instructions that, when executed, cause the data analysis platform to:

determine, based on the composition of the gas used in the centrifugal compressor, a potential for condensation within the centrifugal compressor; and based on determining the potential for condensation within the centrifugal compressor, send a command configured to cause an adjustment to an operating parameter of the centrifugal compressor.

3. The system of claim 1, comprising:

a mass flow meter among the one or more sensors associated with the centrifugal compressor, wherein the computer-readable memory of the data analysis platform stores executable instructions that, when executed, cause the data analysis platform to:

receive density information associated with the centrifugal compressor and collected by the mass flow meter; and analyze the density information to determine the composition of the gas used in the centrifugal compressor.

4. The system of claim 1, wherein the computer-readable memory of the data analysis platform stores executable instructions that, when executed, cause the data analysis platform to:

using the sensor data associated with the centrifugal compressor, model conditions within the centrifugal compressor; and based on modeling the conditions within the centrifugal compressor, predict whether condensation will occur in the centrifugal compressor.

5. The system of claim 4, wherein the computer-readable memory of the data analysis platform stores executable instructions that, when executed, cause the data analysis platform to:

based on modeling the conditions within the centrifugal compressor, predict an amount of the predicted condensation in the centrifugal compressor.

6. The system of claim 4, wherein the computer-readable memory of the data analysis platform stores executable instructions that, when executed, cause the data analysis platform to:

based on modeling the conditions within the centrifugal compressor, predict a dew point of the gas used in the centrifugal compressor.

7. The system of claim 1, comprising:

a thermal mass meter among the one or more sensors associated with the centrifugal compressor, wherein the computer-readable memory of the data analysis platform stores executable instructions that, when executed, cause the data analysis platform to:

receive heat capacity information associated with the centrifugal compressor and collected by the thermal mass meter; and analyze the heat capacity information to determine the composition of the gas used in the centrifugal compressor.

8. The system of claim 1, wherein the computer-readable memory of the data analysis platform stores executable instructions that, when executed, cause the data analysis platform to:

determine, based on the composition of the gas used in the centrifugal compressor, a potential seal failure of the dry gas seal of the centrifugal compressor.

9. The system of claim 1 wherein the computer-readable memory of the data analysis platform stores executable instructions that, when executed, cause the data analysis platform to:

compare the amount of heavy gas in the gas used in the centrifugal compressor to different operational data associated with the centrifugal compressor.

10. One or more non-transitory computer-readable media storing executable instructions that, when executed, cause a data analysis platform to:

receive sensor data associated with a centrifugal compressor and collected by one or more sensors associated with the centrifugal compressor;

analyze the sensor data comprising temperature information associated with the centrifugal compressor to determine a composition of gas used in the centrifugal compressor;

determine, based on the composition of the gas used in the centrifugal compressor, a potential component failure of the centrifugal compressor;

based on determining the potential component failure of the centrifugal compressor, send a command configured to cause an adjustment to an operating parameter of the centrifugal compressor;

using the sensor data associated with the centrifugal compressor, model conditions within the centrifugal compressor; and based on modeling the conditions within the centrifugal compressor, predict whether condensation will occur in the centrifugal compressor.

11. The one or more non-transitory computer-readable media of claim 10, storing executable instructions that, when executed, cause the data analysis platform to:

determine, based on the composition of the gas used in the centrifugal compressor, a potential for condensation within the centrifugal compressor; and based on determining the potential for condensation within the centrifugal compressor, send a command configured to cause an adjustment to an operating parameter of the centrifugal compressor.

12. The one or more non-transitory computer-readable media of claim 10, storing executable instructions that, when executed, cause the data analysis platform to:

based on modeling the conditions within the centrifugal compressor, predict an amount of the predicted condensation in the centrifugal compressor.

13. The one or more non-transitory computer-readable media of claim 10, storing executable instructions that, when executed, cause the data analysis platform to:
based on modeling the conditions within the centrifugal compressor, predict a dew point of the gas used in the centrifugal compressor.

14. The one or more non-transitory computer-readable media of claim 10, storing executable instructions that, when executed, cause the data analysis platform to:
determine, based on the composition of the gas used in the centrifugal compressor, a potential seal failure of a dry gas seal of the centrifugal compressor.

15. A method comprising:
receiving, by a data analysis computing device, sensor data associated with a centrifugal compressor and collected by one or more sensors associated with the centrifugal compressor;
analyzing, by the data analysis computing device, the sensor data comprising temperature information associated with the centrifugal compressor to determine a composition of gas used in the centrifugal compressor;
determining, by the data analysis computing device and based on the composition of the gas used in the centrifugal compressor, a potential component failure of the centrifugal compressor;
based on determining the potential component failure of the centrifugal compressor, sending, by the data analysis computing device, a command configured to cause an adjustment to an operating parameter of the centrifugal compressor;
using the sensor data associated with the centrifugal compressor, modeling conditions within the centrifugal compressor;
based on modeling the conditions within the centrifugal compressor, predicting, by the data analysis computing device, whether condensation will occur in the centrifugal compressor;
predicting, by the data analysis computing device, an amount of the predicted condensation in the centrifugal compressor; and
predicting, by the data analysis computing device, a dew point of the gas used in the centrifugal compressor.

16. The method of claim 15, comprising:
determining, by the data analysis computing device and based on the composition of the gas used in the centrifugal compressor, a potential for condensation within the centrifugal compressor; and
based on determining the potential for condensation within the centrifugal compressor, sending, by the data analysis computing device, a command configured to cause an adjustment to an operating parameter of the centrifugal compressor.

17. The method of claim 15, comprising:
determining, by the data analysis computing device and based on the composition of the gas used in the centrifugal compressor, a potential seal failure of a dry gas seal of the centrifugal compressor.

* * * * *